(12) United States Patent
Bermudes

(10) Patent No.: US 9,739,773 B1
(45) Date of Patent: *Aug. 22, 2017

(54) COMPOSITIONS AND METHODS FOR DETERMINING SUCCESSFUL IMMUNIZATION BY ONE OR MORE VACCINES

(71) Applicant: David Gordon Bermudes, Woodland Hills, CA (US)

(72) Inventor: David Gordon Bermudes, Woodland Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/623,956

(22) Filed: Feb. 17, 2015

(51) Int. Cl.
| | |
|---|---|
| *G01N 33/53* | (2006.01) |
| *G01N 33/538* | (2006.01) |
| *G01N 33/536* | (2006.01) |
| *G01N 33/563* | (2006.01) |
| *G01N 33/558* | (2006.01) |
| *G01N 33/68* | (2006.01) |

(52) U.S. Cl.
CPC ....... *G01N 33/558* (2013.01); *G01N 33/6854* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 3,410,839 A | 11/1968 | De et al. | |
| 3,420,205 A | 1/1969 | Morison et al. | |
| 3,620,677 A | 11/1971 | Morison et al. | |
| 3,666,421 A | 5/1972 | Price et al. | |
| 3,811,840 A | 5/1974 | Bauer et al. | |
| 3,850,752 A | 11/1974 | Schuurs et al. | |
| 3,876,504 A | 4/1975 | Koffler | |
| 3,915,647 A | 10/1975 | Wright | |
| 3,954,564 A | 5/1976 | Mennen | |
| 4,022,876 A | 5/1977 | Anbar | |
| 4,042,335 A | 8/1977 | Clement | |
| 4,059,407 A | 11/1977 | Hochstrasser | |

(Continued)

FOREIGN PATENT DOCUMENTS

| | | |
|---|---|---|
| DE | 19502375 A1 | 8/1996 |
| DE | 19502375 C2 | 6/2000 |

(Continued)

*Primary Examiner* — Janet L Andres
*Assistant Examiner* — M. Franco Salvoza
(74) *Attorney, Agent, or Firm* — Steven M. Hoffberg, Esq.; Ostrolenk Faber LLP

(57) ABSTRACT

A host antigen-specific antibody testing system and method. The a ternary complex of the antigen, a ligand-bound anti-host IgM, and a non-host anti-antigen IgG detector conjugate selectively form a quaternary complex with host antibodies, wherein the host antibodies and IgG compete for the antigen, and the anti-host IgM binds the host antibodies. The quaternary complex is retained by an immobilized IgM ligand binding agent, and any residual ternary complex is retained by a later encountered immobilized anti-non-host IgG. If sufficient host antibodies have a high affinity for the antigen, the complex is detected at the quaternary complex detection region based on the presence of the detector, and if there are insufficient high affinity host antibodies, the ternary complex migrates past the quaternary complex detection region and is retained and detected at a control region.

20 Claims, 4 Drawing Sheets

Figure 1A:
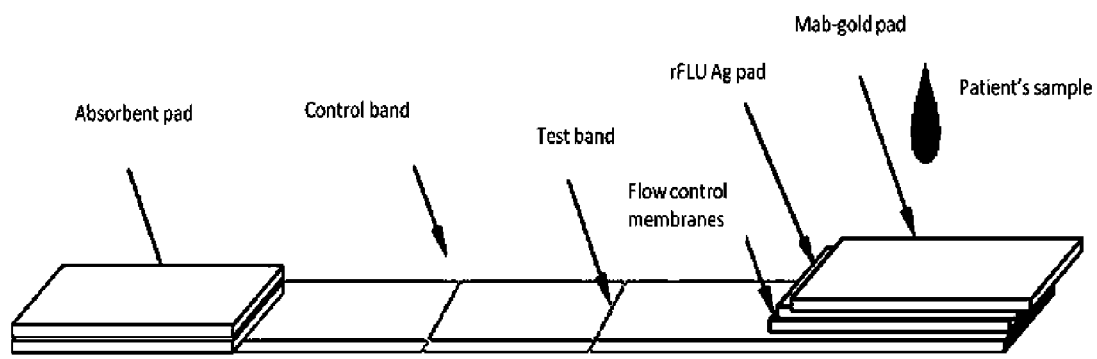

| | Positive Test | Negative Test | Invalid Test | Invalid Test |
|---|---|---|---|---|
| Strip Assay Test | | | | |
| Control Band | + | + | - | - |
| Test Band | + | - | - | - |

(56) References Cited

U.S. PATENT DOCUMENTS

| | | |
|---|---|---|
| 4,067,959 A | 1/1978 | Bolz |
| 4,071,315 A | 1/1978 | Chateau |
| 4,090,888 A | 5/1978 | Rademachers et al. |
| 4,094,647 A | 6/1978 | Deutsch et al. |
| 4,122,030 A | 10/1978 | Smith et al. |
| 4,166,105 A | 8/1979 | Hirschfeld |
| 4,168,146 A | 9/1979 | Grubb et al. |
| 4,169,138 A | 9/1979 | Jonsson |
| 4,184,920 A | 1/1980 | Blixt et al. |
| 4,208,479 A | 6/1980 | Zuk et al. |
| 4,230,797 A | 10/1980 | Boguslaski et al. |
| 4,233,402 A | 11/1980 | Maggio et al. |
| 4,235,601 A | 11/1980 | Deutsch et al. |
| 4,244,940 A | 1/1981 | Jeong et al. |
| 4,246,339 A | 1/1981 | Cole et al. |
| 4,253,844 A | 3/1981 | Limet et al. |
| 4,254,096 A | 3/1981 | Monthony et al. |
| 4,299,916 A | 11/1981 | Litman et al. |
| 4,301,139 A | 11/1981 | Feingers et al. |
| 4,302,536 A | 11/1981 | Longenecker |
| 4,313,734 A | 2/1982 | Leuvering |
| 4,315,907 A | 2/1982 | Fridlender et al. |
| 4,315,908 A | 2/1982 | Zer et al. |
| 4,318,707 A | 3/1982 | Litman et al. |
| 4,332,788 A | 6/1982 | Mochida et al. |
| 4,361,537 A | 11/1982 | Deutsch et al. |
| 4,366,241 A | 12/1982 | Tom et al. |
| 4,366,243 A | 12/1982 | Rupchock et al. |
| 4,373,932 A | 2/1983 | Gribnau et al. |
| 4,374,925 A | 2/1983 | Litman et al. |
| 4,376,110 A | 3/1983 | David et al. |
| 4,391,904 A | 7/1983 | Litman et al. |
| 4,415,700 A | 11/1983 | Batz et al. |
| 4,435,504 A | 3/1984 | Zuk et al. |
| 4,442,204 A | 4/1984 | Greenquist et al. |
| 4,446,231 A | 5/1984 | Self |
| 4,446,232 A | 5/1984 | Liotta |
| 4,447,526 A | 5/1984 | Rupchock et al. |
| 4,452,901 A | 6/1984 | Gordon et al. |
| 4,461,829 A | 7/1984 | Greenquist |
| 4,472,498 A | 9/1984 | Masuda et al. |
| 4,477,575 A | 10/1984 | Vogel et al. |
| 4,493,793 A | 1/1985 | Chu |
| 4,514,508 A | 4/1985 | Hirschfeld |
| 4,518,565 A | 5/1985 | Boger et al. |
| 4,552,839 A | 11/1985 | Gould et al. |
| 4,578,399 A | 3/1986 | Schorlemmer et al. |
| 4,587,102 A | 5/1986 | Nagatomo et al. |
| 4,594,327 A | 6/1986 | Zuk |
| 4,595,655 A | 6/1986 | Self |
| 4,595,656 A | 6/1986 | Allen et al. |
| 4,608,246 A | 8/1986 | Bayer et al. |
| 4,624,804 A | 11/1986 | Voelter et al. |
| 4,624,929 A | 11/1986 | Ullman |
| 4,629,690 A | 12/1986 | Weng et al. |
| 4,632,901 A | 12/1986 | Valkirs et al. |
| 4,659,678 A | 4/1987 | Forrest et al. |
| 4,665,018 A | 5/1987 | Vold |
| 4,670,381 A | 6/1987 | Frickey et al. |
| 4,678,757 A | 7/1987 | Rapkin et al. |
| 4,695,554 A | 9/1987 | O'Connell et al. |
| 4,696,797 A | 9/1987 | Kelton |
| 4,697,797 A | 10/1987 | Gold |
| 4,703,017 A | 10/1987 | Campbell et al. |
| 4,707,450 A | 11/1987 | Nason |
| 4,725,406 A | 2/1988 | Compton et al. |
| 4,727,019 A | 2/1988 | Valkirs et al. |
| 4,740,468 A | 4/1988 | Weng et al. |
| 4,742,011 A | 5/1988 | Blake et al. |
| 4,749,647 A | 6/1988 | Thomas et al. |
| 4,753,776 A | 6/1988 | Hillman et al. |
| 4,757,004 A | 7/1988 | Houts et al. |
| 4,770,853 A | 9/1988 | Bernstein |
| 4,775,515 A | 10/1988 | Cottingham |
| 4,775,636 A | 10/1988 | Moeremans et al. |
| 4,777,964 A | 10/1988 | Briggs et al. |
| 4,780,422 A | 10/1988 | Mitani et al. |
| 4,786,589 A | 11/1988 | Rounds |
| 4,786,594 A | 11/1988 | Khanna et al. |
| 4,786,606 A | 11/1988 | Giegel et al. |
| 4,788,152 A | 11/1988 | Doeding et al. |
| 4,790,979 A | 12/1988 | Terminiello et al. |
| 4,791,056 A | 12/1988 | Sizto et al. |
| 4,803,170 A | 2/1989 | Stanton et al. |
| 4,806,311 A | 2/1989 | Greenquist |
| 4,806,312 A | 2/1989 | Greenquist |
| 4,810,470 A | 3/1989 | Burkhardt et al. |
| 4,816,224 A | 3/1989 | Vogel et al. |
| 4,816,392 A | 3/1989 | Hokama |
| 4,818,677 A | 4/1989 | Hay-Kaufman et al. |
| 4,824,784 A | 4/1989 | Cantarow |
| 4,837,145 A | 6/1989 | Liotta |
| 4,837,168 A | 6/1989 | de Jaeger et al. |
| 4,843,000 A | 6/1989 | Litman et al. |
| 4,849,338 A | 7/1989 | Litman et al. |
| 4,853,335 A | 8/1989 | Olsen et al. |
| 4,855,240 A | 8/1989 | Rosenstein et al. |
| 4,857,453 A | 8/1989 | Ullman et al. |
| 4,859,612 A | 8/1989 | Cole et al. |
| 4,861,552 A | 8/1989 | Masuda et al. |
| 4,861,711 A | 8/1989 | Friesen et al. |
| 4,868,106 A | 9/1989 | Ito et al. |
| 4,868,108 A | 9/1989 | Bahar et al. |
| 4,870,005 A | 9/1989 | Akiyoshi et al. |
| 4,874,691 A | 10/1989 | Chandler |
| 4,879,215 A | 11/1989 | Weng et al. |
| 4,900,663 A | 2/1990 | Wie et al. |
| 4,906,439 A | 3/1990 | Grenner |
| 4,910,150 A | 3/1990 | Doeding et al. |
| 4,914,040 A | 4/1990 | Lenz et al. |
| 4,916,056 A | 4/1990 | Brown, III et al. |
| 4,920,046 A | 4/1990 | McFarland et al. |
| 4,929,544 A | 5/1990 | Vold |
| 4,931,385 A | 6/1990 | Block et al. |
| 4,933,092 A | 6/1990 | Aunet et al. |
| 4,940,456 A | 7/1990 | Sibalis et al. |
| 4,943,522 A | 7/1990 | Eisinger et al. |
| 4,943,552 A | 7/1990 | Osajima et al. |
| 4,945,045 A | 7/1990 | Forrest et al. |
| 4,954,452 A | 9/1990 | Yost et al. |
| 4,956,275 A | 9/1990 | Zuk et al. |
| 4,956,302 A | 9/1990 | Gordon et al. |
| 4,956,303 A | 9/1990 | Self |
| 4,959,305 A | 9/1990 | Woodrum |
| 4,959,307 A | 9/1990 | Olson |
| 4,960,691 A | 10/1990 | Gordon et al. |
| 4,978,610 A | 12/1990 | Forrest et al. |
| 4,981,786 A | 1/1991 | Dafforn et al. |
| 4,987,085 A | 1/1991 | Allen et al. |
| 4,990,442 A | 2/1991 | Del Campo |
| 4,994,373 A | 2/1991 | Stavrianopoulos et al. |
| 5,008,080 A | 4/1991 | Brown, III et al. |
| 5,019,496 A | 5/1991 | Oster et al. |
| 5,026,653 A | 6/1991 | Lee et al. |
| 5,028,535 A | 7/1991 | Buechler et al. |
| 5,030,558 A | 7/1991 | Litman et al. |
| 5,035,997 A | 7/1991 | Oster et al. |
| 5,059,522 A | 10/1991 | Wayne |
| 5,073,340 A | 12/1991 | Covington et al. |
| 5,073,484 A | 12/1991 | Swanson et al. |
| 5,079,142 A | 1/1992 | Coleman et al. |
| 5,085,987 A | 2/1992 | Olson |
| 5,085,988 A | 2/1992 | Olson |
| 5,089,391 A | 2/1992 | Buechler et al. |
| 5,089,394 A | 2/1992 | Chun et al. |
| 5,091,318 A | 2/1992 | Anawis et al. |
| 5,096,833 A | 3/1992 | Lau et al. |
| 5,102,788 A | 4/1992 | Cole |
| 5,103,836 A | 4/1992 | Goldstein et al. |
| 5,104,793 A | 4/1992 | Buck |
| 5,120,504 A | 6/1992 | Petro-Roy et al. |
| 5,120,643 A | 6/1992 | Ching et al. |
| 5,135,719 A | 8/1992 | Hillman et al. |
| 5,137,804 A | 8/1992 | Greene et al. |

(56) References Cited

U.S. PATENT DOCUMENTS

| | | |
|---|---|---|
| 5,137,808 A | 8/1992 | Ullman et al. |
| 5,139,685 A | 8/1992 | de Castro et al. |
| 5,141,850 A | 8/1992 | Cole et al. |
| 5,141,875 A | 8/1992 | Kelton et al. |
| 5,142,031 A | 8/1992 | Lee et al. |
| 5,143,852 A | 9/1992 | Valkirs et al. |
| 5,145,789 A | 9/1992 | Corti et al. |
| 5,149,622 A | 9/1992 | Brown et al. |
| 5,149,630 A | 9/1992 | Forrest et al. |
| 5,156,952 A | 10/1992 | Litman et al. |
| 5,156,953 A | 10/1992 | Litman et al. |
| 5,158,869 A | 10/1992 | Pouletty et al. |
| 5,160,701 A | 11/1992 | Brown, III et al. |
| 5,166,051 A | 11/1992 | Killeen et al. |
| 5,171,688 A | 12/1992 | Hewett et al. |
| 5,177,021 A | 1/1993 | Kondo |
| 5,183,740 A | 2/1993 | Ligler et al. |
| 5,185,245 A | 2/1993 | Heimer |
| 5,188,938 A | 2/1993 | Khanna et al. |
| 5,196,302 A | 3/1993 | Kidwell |
| 5,196,306 A | 3/1993 | Bobrow et al. |
| 5,200,312 A | 4/1993 | Oprandy |
| 5,200,321 A | 4/1993 | Kidwell |
| 5,202,233 A | 4/1993 | Herrmann et al. |
| 5,206,136 A | 4/1993 | Monji et al. |
| 5,206,177 A | 4/1993 | DeLaCroix et al. |
| 5,212,065 A | 5/1993 | Pegg et al. |
| 5,225,330 A | 7/1993 | Ginsburg et al. |
| 5,232,830 A | 8/1993 | Van Ness |
| 5,232,835 A | 8/1993 | Litman et al. |
| RE34,405 E | 10/1993 | Gould et al. |
| 5,250,412 A | 10/1993 | Giegel |
| 5,258,163 A | 11/1993 | Krause et al. |
| 5,260,193 A | 11/1993 | Olson |
| 5,260,221 A | 11/1993 | Ramel et al. |
| 5,260,428 A | 11/1993 | Herrmann et al. |
| 5,262,067 A | 11/1993 | Wilk et al. |
| 5,292,636 A | 3/1994 | Kung et al. |
| 5,308,775 A | 5/1994 | Donovan et al. |
| 5,335,673 A | 8/1994 | Goldstein et al. |
| 5,340,539 A | 8/1994 | Allen et al. |
| 5,342,759 A | 8/1994 | Litman et al. |
| 5,352,582 A | 10/1994 | Lichtenwalter et al. |
| 5,354,692 A | 10/1994 | Yang et al. |
| 5,356,782 A | 10/1994 | Moorman et al. |
| 5,364,533 A | 11/1994 | Ogura et al. |
| 5,369,007 A | 11/1994 | Kidwell |
| 5,374,524 A | 12/1994 | Miller |
| 5,376,337 A | 12/1994 | Seymour |
| 5,384,264 A | 1/1995 | Chen et al. |
| 5,391,272 A | 2/1995 | O'Daly et al. |
| 5,391,478 A | 2/1995 | Greene et al. |
| 5,401,634 A | 3/1995 | Milbrath |
| 5,418,171 A | 5/1995 | Kimura et al. |
| 5,423,989 A | 6/1995 | Allen et al. |
| 5,424,193 A | 6/1995 | Pronovost et al. |
| 5,435,970 A | 7/1995 | Mamenta et al. |
| 5,437,983 A | 8/1995 | Watts et al. |
| 5,443,953 A | 8/1995 | Hansen et al. |
| 5,460,978 A | 10/1995 | Martin et al. |
| 5,468,622 A | 11/1995 | Richards |
| 5,468,648 A | 11/1995 | Chandler |
| 5,474,911 A | 12/1995 | Pontius |
| 5,478,729 A | 12/1995 | Van Atta et al. |
| 5,480,792 A | 1/1996 | Buechler et al. |
| 5,494,646 A | 2/1996 | Seymour |
| 5,501,949 A | 3/1996 | Marshall |
| 5,507,410 A | 4/1996 | Clark et al. |
| 5,521,102 A | 5/1996 | Boehringer et al. |
| 5,521,289 A | 5/1996 | Hainfeld et al. |
| 5,527,686 A | 6/1996 | Fitzpatrick et al. |
| 5,529,904 A | 6/1996 | Ginsburg et al. |
| 5,536,471 A | 7/1996 | Clark et al. |
| 5,540,890 A | 7/1996 | Clark et al. |
| 5,541,115 A | 7/1996 | Siegel et al. |
| 5,550,032 A | 8/1996 | Isbister |
| 5,556,756 A | 9/1996 | Olsen et al. |
| 5,558,834 A | 9/1996 | Chu et al. |
| 5,559,041 A | 9/1996 | Kang et al. |
| 5,573,919 A | 11/1996 | Kearns et al. |
| 5,575,978 A | 11/1996 | Clark et al. |
| 5,578,459 A | 11/1996 | Gordon et al. |
| 5,578,494 A | 11/1996 | Clark et al. |
| 5,580,561 A | 12/1996 | Cercek et al. |
| 5,580,790 A | 12/1996 | Wall et al. |
| 5,583,001 A | 12/1996 | Bobrow et al. |
| 5,591,645 A | 1/1997 | Rosenstein |
| 5,602,040 A | 2/1997 | May et al. |
| 5,605,665 A | 2/1997 | Clark et al. |
| 5,607,863 A | 3/1997 | Chandler |
| 5,610,069 A | 3/1997 | Clark et al. |
| 5,620,845 A | 4/1997 | Gould et al. |
| 5,620,859 A | 4/1997 | Garry et al. |
| 5,622,871 A | 4/1997 | May et al. |
| 5,627,522 A | 5/1997 | Walker et al. |
| 5,635,362 A | 6/1997 | Levine et al. |
| 5,635,364 A | 6/1997 | Clark et al. |
| 5,635,603 A | 6/1997 | Hansen et al. |
| 5,637,468 A | 6/1997 | Mason |
| 5,646,049 A | 7/1997 | Tayi |
| 5,650,333 A | 7/1997 | Holtlund et al. |
| 5,654,162 A | 8/1997 | Guire et al. |
| 5,654,401 A | 8/1997 | Clements et al. |
| 5,656,502 A | 8/1997 | MacKay et al. |
| 5,656,503 A | 8/1997 | May et al. |
| 5,663,303 A | 9/1997 | Rochette-Egly et al. |
| 5,665,534 A | 9/1997 | Vandenbergh et al. |
| 5,667,976 A | 9/1997 | Van Ness et al. |
| 5,679,526 A | 10/1997 | Buechler et al. |
| 5,686,315 A | 11/1997 | Pronovost et al. |
| 5,691,207 A | 11/1997 | Holtlund et al. |
| 5,703,207 A | 12/1997 | Martin et al. |
| 5,707,820 A | 1/1998 | Wilsey et al. |
| 5,712,170 A | 1/1998 | Kouvonen et al. |
| 5,712,172 A | 1/1998 | Huang et al. |
| 5,714,389 A | 2/1998 | Charlton et al. |
| 5,716,778 A | 2/1998 | Weng et al. |
| 5,723,345 A | 3/1998 | Yamauchi et al. |
| 5,725,774 A | 3/1998 | Neyer |
| 5,726,010 A | 3/1998 | Clark |
| 5,726,013 A | 3/1998 | Clark |
| 5,728,587 A | 3/1998 | Kang et al. |
| 5,728,590 A | 3/1998 | Powell |
| 5,731,158 A | 3/1998 | Bobrow et al. |
| 5,739,041 A | 4/1998 | Nazareth et al. |
| 5,741,652 A | 4/1998 | Shibuya et al. |
| 5,747,254 A | 5/1998 | Pontius |
| 5,750,333 A | 5/1998 | Clark |
| 5,759,794 A | 6/1998 | Levine et al. |
| 5,762,878 A | 6/1998 | Clark et al. |
| 5,763,262 A | 6/1998 | Wong et al. |
| 5,766,886 A | 6/1998 | Studnicka et al. |
| 5,766,961 A | 6/1998 | Pawlak et al. |
| 5,770,196 A | 6/1998 | Studnicka |
| 5,770,395 A | 6/1998 | Isbister |
| 5,770,460 A | 6/1998 | Pawlak et al. |
| 5,776,710 A | 7/1998 | Levine et al. |
| 5,789,154 A | 8/1998 | Durst et al. |
| 5,798,215 A | 8/1998 | Cathey et al. |
| 5,811,525 A | 9/1998 | Rittershaus |
| 5,817,473 A | 10/1998 | Das et al. |
| 5,820,826 A | 10/1998 | Moorman |
| 5,821,073 A | 10/1998 | Lee |
| 5,821,123 A | 10/1998 | Studnicka |
| 5,833,923 A | 11/1998 | McClintock et al. |
| 5,833,924 A | 11/1998 | McClintock et al. |
| 5,834,215 A | 11/1998 | Garry et al. |
| 5,834,217 A | 11/1998 | Levine et al. |
| 5,843,680 A | 12/1998 | Manian et al. |
| 5,843,794 A | 12/1998 | Singer |
| 5,846,838 A | 12/1998 | Chandler |
| 5,866,322 A | 2/1999 | Jou et al. |
| 5,866,363 A | 2/1999 | Pieczenik |
| 5,869,345 A | 2/1999 | Chandler |

(56) References Cited

U.S. PATENT DOCUMENTS

| | | |
|---|---|---|
| 5,869,619 A | 2/1999 | Studnicka |
| 5,872,221 A | 2/1999 | Martin et al. |
| 5,877,028 A | 3/1999 | Chandler et al. |
| 5,879,881 A | 3/1999 | Rubenstein |
| 5,879,951 A | 3/1999 | Sy |
| 5,900,379 A | 5/1999 | Noda et al. |
| 5,916,521 A | 6/1999 | Bunce et al. |
| 5,929,049 A | 7/1999 | Singh et al. |
| 5,932,174 A | 8/1999 | Brayton et al. |
| 5,939,252 A | 8/1999 | Lennon et al. |
| 5,939,272 A | 8/1999 | Buechler et al. |
| 5,939,331 A | 8/1999 | Burd et al. |
| 5,942,407 A | 8/1999 | Liotta et al. |
| 5,962,336 A | 10/1999 | Sun |
| 5,965,458 A | 10/1999 | Kouvonen et al. |
| 5,976,824 A | 11/1999 | Gordon |
| 5,985,579 A | 11/1999 | Buechler et al. |
| 5,989,921 A | 11/1999 | Charlton et al. |
| 5,998,220 A | 12/1999 | Chandler |
| 5,998,221 A | 12/1999 | Malick et al. |
| 6,001,658 A | 12/1999 | Fredrickson |
| 6,007,999 A | 12/1999 | Clark |
| 6,008,056 A | 12/1999 | Thieme |
| 6,008,059 A | 12/1999 | Schrier et al. |
| 6,017,698 A | 1/2000 | Bienhaus et al. |
| 6,017,767 A | 1/2000 | Chandler |
| 6,025,477 A | 2/2000 | Calenoff |
| 6,027,904 A | 2/2000 | Devine et al. |
| 6,030,773 A | 2/2000 | Agnello |
| 6,046,057 A | 4/2000 | Nazareth et al. |
| 6,046,058 A | 4/2000 | Sun |
| 6,060,237 A | 5/2000 | Nygren et al. |
| 6,084,092 A | 7/2000 | Wakshull et al. |
| 6,086,748 A | 7/2000 | Durst et al. |
| 6,096,561 A | 8/2000 | Tayi |
| 6,100,099 A | 8/2000 | Gordon et al. |
| 6,121,425 A | 9/2000 | Hainfeld et al. |
| 6,132,682 A | 10/2000 | Christner et al. |
| 6,133,227 A | 10/2000 | Barnabas et al. |
| 6,136,549 A | 10/2000 | Feistel |
| 6,140,136 A | 10/2000 | Lee |
| 6,146,589 A | 11/2000 | Chandler |
| 6,153,147 A | 11/2000 | Craig |
| 6,156,271 A | 12/2000 | May |
| 6,156,742 A | 12/2000 | Mackenzie |
| 6,165,796 A | 12/2000 | Bell |
| 6,168,956 B1 | 1/2001 | Chandler |
| 6,171,801 B1 | 1/2001 | Staples et al. |
| 6,187,598 B1 | 2/2001 | May et al. |
| 6,190,617 B1 | 2/2001 | Clark et al. |
| 6,194,222 B1 | 2/2001 | Buechler et al. |
| 6,194,225 B1 | 2/2001 | Oka et al. |
| 6,197,598 B1 | 3/2001 | Schrier et al. |
| 6,210,898 B1 | 4/2001 | Bouma et al. |
| 6,225,074 B1 | 5/2001 | Wright et al. |
| 6,228,602 B1 | 5/2001 | Pugia |
| 6,228,660 B1 | 5/2001 | May et al. |
| 6,245,296 B1 | 6/2001 | Ligler et al. |
| 6,245,577 B1 | 6/2001 | McVicker et al. |
| 6,248,596 B1 | 6/2001 | Durst et al. |
| 6,262,264 B1 | 7/2001 | Buck, Jr. et al. |
| 6,271,044 B1 | 8/2001 | Ballerstadt et al. |
| 6,277,647 B1 | 8/2001 | Christner et al. |
| 6,277,650 B1 | 8/2001 | Nazareth et al. |
| 6,284,194 B1 | 9/2001 | Chu |
| 6,294,062 B1 | 9/2001 | Buck, Jr. et al. |
| 6,294,321 B1 | 9/2001 | Wakshull et al. |
| 6,297,020 B1 | 10/2001 | Brock |
| 6,306,614 B1 | 10/2001 | Romaschin et al. |
| 6,319,676 B1 | 11/2001 | Nazareth et al. |
| 6,325,980 B1 | 12/2001 | Christner et al. |
| 6,326,139 B1 | 12/2001 | Soreq et al. |
| 6,335,205 B1 | 1/2002 | Bausback |
| 6,352,824 B1 | 3/2002 | Buck, Jr. et al. |
| 6,352,862 B1 | 3/2002 | Davis et al. |
| 6,355,429 B1 | 3/2002 | Nygren et al. |
| 6,358,752 B1 | 3/2002 | Durst et al. |
| 6,365,417 B1 | 4/2002 | Fleming et al. |
| 6,368,876 B1 | 4/2002 | Huang et al. |
| 6,369,206 B1 | 4/2002 | Leone et al. |
| 6,372,514 B1 | 4/2002 | Lee |
| 6,387,622 B1 | 5/2002 | Siiman et al. |
| 6,403,298 B1 | 6/2002 | Lee et al. |
| 6,403,384 B1 | 6/2002 | Lea |
| 6,413,473 B1 | 7/2002 | Bacon |
| 6,413,715 B2 | 7/2002 | Wakshull et al. |
| 6,416,962 B1 | 7/2002 | Das et al. |
| 6,416,975 B1 | 7/2002 | Gallagher et al. |
| 6,436,649 B1 | 8/2002 | Kohl et al. |
| 6,485,982 B1 | 11/2002 | Charlton |
| 6,489,309 B1 | 12/2002 | Singh et al. |
| 6,509,196 B1 | 1/2003 | Brooks et al. |
| 6,514,769 B2 | 2/2003 | Lee |
| 6,528,325 B1 | 3/2003 | Hubscher et al. |
| 6,534,008 B1 | 3/2003 | Angros |
| 6,534,320 B2 | 3/2003 | Ching et al. |
| 6,537,828 B1 | 3/2003 | Nakaya et al. |
| 6,541,277 B1 | 4/2003 | Kang et al. |
| 6,551,834 B2 | 4/2003 | Carpenter et al. |
| 6,558,959 B2 | 5/2003 | Chu |
| 6,576,460 B1 | 6/2003 | Baeumner et al. |
| 6,605,448 B1 | 8/2003 | Pieczenik |
| 6,627,459 B1 | 9/2003 | Tung et al. |
| 6,635,469 B1 | 10/2003 | Litt et al. |
| 6,649,830 B1 | 11/2003 | Bartlett et al. |
| 6,656,744 B2 | 12/2003 | Pronovost et al. |
| 6,660,534 B2 | 12/2003 | McVicker et al. |
| 6,689,317 B1 | 2/2004 | Rees |
| 6,699,722 B2 | 3/2004 | Bauer et al. |
| 6,713,271 B1 | 3/2004 | Feistel |
| 6,723,840 B1 | 4/2004 | Sakowicz et al. |
| 6,730,268 B2 | 5/2004 | Lee et al. |
| 6,733,983 B1 | 5/2004 | Houthoff et al. |
| 6,764,830 B1 | 7/2004 | Sakowicz et al. |
| 6,767,710 B2 | 7/2004 | DiNello et al. |
| 6,767,714 B2 | 7/2004 | Nazareth et al. |
| 6,808,889 B2 | 10/2004 | Fitzpatrick et al. |
| 6,815,169 B1 | 11/2004 | Sakowicz et al. |
| 6,818,455 B2 | 11/2004 | May et al. |
| 6,824,975 B2 | 11/2004 | Hubscher et al. |
| 6,828,110 B2 | 12/2004 | Lee et al. |
| 6,841,159 B2 | 1/2005 | Simonson |
| 6,855,292 B2 | 2/2005 | Angros |
| 6,855,561 B2 | 2/2005 | Jerome et al. |
| 6,887,669 B1 | 5/2005 | Staples et al. |
| 6,905,816 B2 | 6/2005 | Jacobs et al. |
| 6,924,153 B1 * | 8/2005 | Boehringer .......... G01N 33/558 <br> 422/420 |
| 6,949,524 B2 | 9/2005 | Singh et al. |
| 6,991,912 B2 | 1/2006 | Feistel |
| 7,026,449 B2 | 4/2006 | Baker et al. |
| 7,045,310 B2 | 5/2006 | Buck, Jr. et al. |
| 7,045,342 B2 | 5/2006 | Nazareth et al. |
| 7,052,831 B2 | 5/2006 | Fletcher et al. |
| 7,064,197 B1 | 6/2006 | Rabbani et al. |
| 7,144,742 B2 | 12/2006 | Boehringer et al. |
| 7,145,019 B2 | 12/2006 | Olejnik et al. |
| 7,169,906 B2 | 1/2007 | Ferrara et al. |
| 7,172,874 B2 | 2/2007 | Hollyfield et al. |
| 7,175,992 B2 | 2/2007 | Fong |
| 7,179,657 B2 | 2/2007 | Jerome et al. |
| 7,189,522 B2 | 3/2007 | Esfandiari |
| RE39,664 E | 5/2007 | Gordon et al. |
| 7,223,535 B2 | 5/2007 | Fields et al. |
| 7,226,793 B2 | 6/2007 | Jerome et al. |
| 7,238,322 B2 | 7/2007 | Wang et al. |
| 7,244,252 B2 | 7/2007 | Berndt |
| 7,247,500 B2 | 7/2007 | Wei et al. |
| 7,250,301 B2 | 7/2007 | Angros |
| 7,252,950 B1 | 8/2007 | Vale et al. |
| 7,270,959 B2 | 9/2007 | Hudak |
| 7,300,627 B1 | 11/2007 | Sun |
| 7,300,633 B2 | 11/2007 | Hudak et al. |
| 7,315,378 B2 | 1/2008 | Phelan et al. |

(56) References Cited

U.S. PATENT DOCUMENTS

| | | |
|---|---|---|
| 7,317,092 B2 | 1/2008 | Ashkenazi et al. |
| 7,317,532 B2 | 1/2008 | Sharrock et al. |
| 7,321,065 B2 | 1/2008 | Scanlan et al. |
| 7,341,839 B2 | 3/2008 | Hollyfield et al. |
| 7,347,972 B1 | 3/2008 | Lee |
| RE40,198 E | 4/2008 | Buck, Jr. et al. |
| 7,355,079 B2 | 4/2008 | Scanlan et al. |
| 7,358,055 B2 | 4/2008 | Valkirs et al. |
| 7,361,473 B2 | 4/2008 | Valkirs et al. |
| 7,371,584 B2 | 5/2008 | Feistel |
| 7,390,626 B2 | 6/2008 | Vojdani |
| 7,390,674 B2 | 6/2008 | Feaster et al. |
| 7,390,675 B2 | 6/2008 | Feistel |
| 7,393,647 B2 | 7/2008 | Valkirs et al. |
| 7,393,656 B2 | 7/2008 | Perez et al. |
| 7,396,689 B2 | 7/2008 | Dowd et al. |
| 7,410,763 B2 | 8/2008 | Su et al. |
| 7,419,796 B2 | 9/2008 | Durst et al. |
| 7,476,362 B2 | 1/2009 | Angros |
| 7,476,502 B2 | 1/2009 | Willey |
| 7,491,551 B2 | 2/2009 | Boehringer et al. |
| 7,498,302 B2 | 3/2009 | Ng et al. |
| 7,507,420 B2 | 3/2009 | Ng et al. |
| 7,517,495 B2 | 4/2009 | Wu et al. |
| 7,517,699 B2 | 4/2009 | Bauer et al. |
| 7,517,903 B2 | 4/2009 | Chen et al. |
| 7,537,937 B2 | 5/2009 | Jerome et al. |
| 7,553,675 B2 | 6/2009 | Jerome et al. |
| 7,560,257 B2 | 7/2009 | Hollyfield et al. |
| 7,560,272 B2 | 7/2009 | Ramsey et al. |
| 7,560,431 B2 | 7/2009 | Zankel et al. |
| 7,563,584 B2 | 7/2009 | Perez et al. |
| 7,566,533 B2 | 7/2009 | Jacobs et al. |
| 7,569,544 B2 | 8/2009 | Zankel et al. |
| 7,572,640 B2 | 8/2009 | Goix et al. |
| 7,595,160 B2 | 9/2009 | White et al. |
| 7,595,198 B2 | 9/2009 | Olejnik et al. |
| 7,622,077 B2 | 11/2009 | Angros |
| 7,622,250 B2 | 11/2009 | Jacobs et al. |
| 7,632,461 B2 | 12/2009 | Angros |
| 7,632,687 B2 | 12/2009 | Gokhan |
| 7,655,184 B2 | 2/2010 | Wang et al. |
| 7,662,643 B2 | 2/2010 | Wei et al. |
| 7,678,760 B2 | 3/2010 | Tang et al. |
| 7,682,801 B2 | 3/2010 | Esfandiari |
| 7,691,595 B2 | 4/2010 | Fong |
| 7,691,962 B2 | 4/2010 | Boyd et al. |
| 7,695,929 B2 | 4/2010 | Kosmeder et al. |
| 7,700,554 B2 | 4/2010 | Beliveau et al. |
| 7,709,215 B2 | 5/2010 | Scuderi |
| 7,713,703 B1 | 5/2010 | Buechler et al. |
| 7,713,709 B2 | 5/2010 | White et al. |
| 7,714,016 B2 | 5/2010 | Gangwar et al. |
| 7,718,388 B2 | 5/2010 | Baeumner |
| 7,736,660 B2 | 6/2010 | Elsemore et al. |
| 7,741,046 B2 | 6/2010 | Larsen et al. |
| 7,754,211 B2 | 7/2010 | Rosenblum et al. |
| 7,763,454 B2 | 7/2010 | Nazareth et al. |
| 7,781,170 B2 | 8/2010 | Tonelli et al. |
| 7,781,209 B2 | 8/2010 | Mancebo et al. |
| 7,781,226 B2 | 8/2010 | McDevitt et al. |
| 7,785,899 B2 | 8/2010 | Saul et al. |
| 7,794,656 B2 | 9/2010 | Liang et al. |
| 7,795,038 B2 | 9/2010 | Jones et al. |
| 7,822,245 B2 | 10/2010 | Wang |
| 7,824,879 B2 | 11/2010 | Khan et al. |
| 7,829,537 B2 | 11/2010 | Zankel et al. |
| 7,829,669 B2 | 11/2010 | Koelsch et al. |
| 7,842,823 B2 | 11/2010 | Chang |
| 7,847,105 B2 | 12/2010 | Gangwar et al. |
| 7,855,054 B2 | 12/2010 | Schneider et al. |
| 7,858,397 B2 | 12/2010 | Durst et al. |
| D631,556 S | 1/2011 | Shi et al. |
| 7,867,780 B2 | 1/2011 | Jones et al. |
| 7,871,568 B2 | 1/2011 | Liang et al. |
| 7,871,781 B2 | 1/2011 | Rundstrom et al. |
| 7,875,433 B2 | 1/2011 | Harris |
| 7,879,293 B2 | 2/2011 | Niedbala et al. |
| 7,879,597 B2 | 2/2011 | Esfandiari |
| 7,885,444 B2 | 2/2011 | Wang |
| 7,888,049 B2 | 2/2011 | Shaari |
| 7,888,470 B2 | 2/2011 | Li et al. |
| 7,897,330 B2 | 3/2011 | Patel et al. |
| 7,914,734 B2 | 3/2011 | Livingston |
| 7,914,999 B2 | 3/2011 | Grenier et al. |
| 7,927,791 B2 | 4/2011 | Welch et al. |
| 7,939,278 B2 | 5/2011 | Perez et al. |
| 7,943,334 B2 | 5/2011 | Akimoto et al. |
| 7,951,547 B2 | 5/2011 | Elsemore et al. |
| 7,964,415 B2 | 6/2011 | Zhelev et al. |
| 7,968,586 B2 | 6/2011 | Gangwar et al. |
| 7,977,317 B2 | 7/2011 | Beliveau et al. |
| 7,977,465 B2 | 7/2011 | Ng et al. |
| 7,993,851 B2 | 8/2011 | Holets-McCormack |
| 7,993,861 B2 | 8/2011 | Elsemore et al. |
| 7,993,862 B2 | 8/2011 | Elsemore et al. |
| 7,995,194 B2 | 8/2011 | Wardlaw et al. |
| 7,998,679 B2 | 8/2011 | Jacobs et al. |
| 8,003,407 B2 | 8/2011 | Zhou et al. |
| 8,007,720 B2 | 8/2011 | Angros |
| 8,007,721 B2 | 8/2011 | Angros |
| 8,021,895 B2 | 9/2011 | Kienle et al. |
| 8,025,850 B2 | 9/2011 | Chan |
| 8,030,091 B2 | 10/2011 | Jerome et al. |
| 8,034,576 B2 | 10/2011 | Bricker et al. |
| 8,034,959 B2 | 10/2011 | Ng et al. |
| 8,052,927 B2 | 11/2011 | Angros |
| 8,062,841 B2 | 11/2011 | Su et al. |
| 8,062,842 B2 | 11/2011 | Vanmechelen et al. |
| 8,067,188 B2 | 11/2011 | Toranto et al. |
| 8,067,241 B2 | 11/2011 | Gerdes et al. |
| 8,067,246 B2 | 11/2011 | Marlborough et al. |
| 8,071,023 B2 | 12/2011 | Angros |
| 8,071,323 B2 | 12/2011 | Dimitrov et al. |
| 8,071,388 B2 | 12/2011 | Huang et al. |
| 8,084,272 B2 | 12/2011 | Campbell et al. |
| 8,092,742 B2 | 1/2012 | Angros |
| 8,097,261 B2 | 1/2012 | Elsemore et al. |
| 8,105,794 B2 | 1/2012 | Shaari |
| 8,105,795 B2 | 1/2012 | Elsemore et al. |
| 8,114,633 B2 | 2/2012 | Weber et al. |
| 8,148,094 B2 | 4/2012 | Nolan et al. |
| 8,178,346 B2 | 5/2012 | Mancebo et al. |
| 8,202,734 B2 | 6/2012 | Jerome et al. |
| 8,206,939 B2 | 6/2012 | Perez et al. |
| 8,221,700 B2 | 7/2012 | Steinmiller et al. |
| 8,264,684 B2 | 9/2012 | Livingston |
| 8,268,574 B2 | 9/2012 | Elsemore et al. |
| 8,268,639 B2 | 9/2012 | Yamashita et al. |
| 8,269,163 B2 | 9/2012 | Pevsner |
| 8,278,421 B2 | 10/2012 | Masat et al. |
| 8,283,127 B2 | 10/2012 | Pfleger et al. |
| 8,287,817 B2 | 10/2012 | Chan |
| 8,288,544 B2 | 10/2012 | Diebold et al. |
| 8,293,904 B2 | 10/2012 | Diebold et al. |
| 8,304,195 B2 | 11/2012 | Hagen et al. |
| 8,309,316 B2 | 11/2012 | Perez et al. |
| 8,309,318 B2 | 11/2012 | Dorval et al. |
| 8,313,694 B2 | 11/2012 | Angros |
| 8,319,954 B2 | 11/2012 | Wardlaw et al. |
| 8,323,903 B2 | 12/2012 | Archer et al. |
| 8,323,914 B2 | 12/2012 | Toranto et al. |
| 8,329,100 B2 | 12/2012 | Angros |
| 8,329,415 B2 | 12/2012 | Holets-McCormack |
| 8,329,647 B2 | 12/2012 | Pfuetzner et al. |
| 8,338,572 B2 | 12/2012 | Scuderi et al. |
| 8,354,058 B2 | 1/2013 | Angros |
| 8,361,734 B2 | 1/2013 | Bricker et al. |
| 8,367,808 B2 | 2/2013 | Elsemore et al. |
| 8,377,864 B2 | 2/2013 | Catelas et al. |
| 8,394,599 B2 | 3/2013 | Perez et al. |
| 8,394,626 B2 | 3/2013 | Ramsey et al. |
| 8,399,403 B2 | 3/2013 | Boyd et al. |
| 8,404,455 B2 | 3/2013 | Li et al. |

(56) References Cited

U.S. PATENT DOCUMENTS

| | | |
|---|---|---|
| 8,415,163 B2 | 4/2013 | Yamashita et al. |
| 8,440,629 B2 | 5/2013 | Starr et al. |
| 8,445,218 B2 | 5/2013 | Pieribone |
| 8,450,072 B2 | 5/2013 | Dodds |
| 8,450,074 B2 | 5/2013 | Dodds |
| 8,455,202 B2 | 6/2013 | Regnier et al. |
| 8,455,203 B2 | 6/2013 | Wang et al. |
| 8,455,263 B2 | 6/2013 | Lee |
| 8,461,117 B2 | 6/2013 | Sufi et al. |
| 8,462,339 B2 | 6/2013 | Livingston |
| 8,476,079 B2 | 7/2013 | Campbell et al. |
| 8,480,975 B2 | 7/2013 | Steinmiller et al. |
| 8,481,690 B2 | 7/2013 | Murthy et al. |
| 8,486,717 B2 | 7/2013 | O'Farrell et al. |
| 8,507,215 B2 | 8/2013 | Salant et al. |
| 8,507,218 B2 | 8/2013 | Heller et al. |
| 8,507,259 B2 | 8/2013 | Esfandiari |
| 8,535,894 B2 | 9/2013 | Archer et al. |
| 8,541,187 B2 | 9/2013 | Passavant et al. |
| 8,557,534 B2 | 10/2013 | Turecek et al. |
| 8,557,604 B2 | 10/2013 | Song |
| 8,557,989 B2 | 10/2013 | Diebold et al. |
| 8,568,719 B2 | 10/2013 | Williamson et al. |
| 8,568,997 B2 | 10/2013 | Pfleger et al. |
| 8,569,462 B2 | 10/2013 | Bedinger et al. |
| 8,574,494 B2 | 11/2013 | Angros |
| 8,580,518 B2 | 11/2013 | Elsemore et al. |
| 8,586,375 B2 | 11/2013 | Chan |
| 8,603,835 B2 | 12/2013 | Esfandiari |
| 8,609,103 B2 | 12/2013 | Zankel et al. |
| 8,617,826 B2 | 12/2013 | Collier et al. |
| 8,623,635 B2 | 1/2014 | Nazareth et al. |
| 8,634,075 B2 | 1/2014 | Livingston |
| 8,642,330 B2 | 2/2014 | Rock et al. |
| 8,658,434 B2 | 2/2014 | Mao et al. |
| 8,664,407 B2 | 3/2014 | Chen et al. |
| 8,673,239 B2 | 3/2014 | Niedbala et al. |
| 8,685,711 B2 | 4/2014 | Goix et al. |
| 8,696,988 B2 | 4/2014 | Angros |
| 8,697,365 B2 | 4/2014 | Grenier et al. |
| 8,703,504 B2 | 4/2014 | Song |
| 8,709,792 B2 | 4/2014 | Saul et al. |
| 8,722,019 B2 | 5/2014 | Jefferies et al. |
| 8,722,395 B2 | 5/2014 | Nazareth et al. |
| 8,735,081 B2 | 5/2014 | Li et al. |
| 8,735,367 B2 | 5/2014 | Heemstra |
| 8,735,546 B2 | 5/2014 | Ghayur et al. |
| 8,741,580 B2 | 6/2014 | Kienle et al. |
| 8,765,437 B2 | 7/2014 | Koppaka et al. |
| 8,791,258 B2 | 7/2014 | Chang |
| 8,795,627 B2 | 8/2014 | Starr et al. |
| 8,802,029 B2 | 8/2014 | Steinmiller et al. |
| 8,815,527 B2 | 8/2014 | Perez et al. |
| 8,828,329 B2 | 9/2014 | Sturman et al. |
| 8,828,665 B2 | 9/2014 | Valdez et al. |
| 8,828,676 B2 | 9/2014 | Weber et al. |
| 8,828,738 B2 | 9/2014 | Campbell et al. |
| 8,835,835 B2 | 9/2014 | Pevsner |
| 8,841,079 B2 | 9/2014 | Scuderi et al. |
| 8,842,264 B2 | 9/2014 | Wardlaw et al. |
| 8,846,320 B2 | 9/2014 | Kosmeder et al. |
| 8,865,420 B2 | 10/2014 | Perez et al. |
| 8,865,458 B2 | 10/2014 | Ramsey et al. |
| 8,865,875 B2 | 10/2014 | Liu et al. |
| 8,877,450 B2 | 11/2014 | Esfandiari |
| 8,883,417 B2 | 11/2014 | Jacobs et al. |
| 8,883,489 B2 | 11/2014 | Pang et al. |
| 8,895,050 B2 | 11/2014 | Tachdjian et al. |
| 8,895,294 B2 | 11/2014 | Elsemore et al. |
| 8,900,881 B2 | 12/2014 | Lee |
| 8,916,389 B2 | 12/2014 | Iwasaki et al. |
| 8,917,392 B2 | 12/2014 | Livingston |
| 8,940,513 B2 | 1/2015 | Koppaka et al. |
| 8,940,866 B2 | 1/2015 | Heller et al. |
| 8,951,736 B2 | 2/2015 | Schmidt |
| 8,951,749 B2 | 2/2015 | Rylatt et al. |
| 8,956,859 B1 | 2/2015 | Bermudes |
| 8,962,263 B2 | 2/2015 | Perez et al. |
| 8,968,678 B2 | 3/2015 | Hu |
| 8,980,572 B2 | 3/2015 | Wong et al. |
| 9,012,393 B2 | 4/2015 | Catelas et al. |
| 9,018,017 B2 | 4/2015 | Campbell et al. |
| 9,034,657 B2 | 5/2015 | Rundstrom et al. |
| 9,040,245 B2 | 5/2015 | Elsemore et al. |
| 9,046,513 B2 | 6/2015 | Ghayur et al. |
| 9,063,129 B2 | 6/2015 | Elsemore et al. |
| 9,063,131 B2 | 6/2015 | Goix et al. |
| 9,063,157 B2 | 6/2015 | Katagiri et al. |
| 9,068,994 B2 | 6/2015 | Collier et al. |
| 9,072,313 B2 | 7/2015 | Shigemura et al. |
| 9,091,684 B2 | 7/2015 | Yerramilli et al. |
| 9,091,686 B2 | 7/2015 | Li et al. |
| 9,102,754 B2 | 8/2015 | Napper et al. |
| 9,103,823 B2 | 8/2015 | Elsemore et al. |
| 9,134,303 B1 | 9/2015 | Koulchin et al. |
| 9,139,642 B2 | 9/2015 | Williamson et al. |
| 9,140,693 B2 | 9/2015 | Ewart et al. |
| 9,145,458 B2 | 9/2015 | Bedinger et al. |
| 9,150,644 B2 | 10/2015 | Dimitrov et al. |
| 9,150,846 B2 | 10/2015 | Jefferies et al. |
| 9,151,747 B1 | 10/2015 | Parente |
| 9,161,992 B2 | 10/2015 | Jefferies et al. |
| 9,164,087 B2 | 10/2015 | Chan |
| 9,176,033 B2 | 11/2015 | Angros |
| 9,193,795 B2 | 11/2015 | Williams |
| 9,199,234 B2 | 12/2015 | Wang et al. |
| 9,200,324 B2 | 12/2015 | Cavet et al. |
| 9,201,065 B2 | 12/2015 | Ruddell et al. |
| 9,201,078 B2 | 12/2015 | Wang et al. |
| 9,207,181 B2 | 12/2015 | Egan et al. |
| 9,212,220 B2 | 12/2015 | Elsemore et al. |
| 9,222,119 B2 | 12/2015 | Heller et al. |
| 9,222,936 B2 | 12/2015 | Schwartz et al. |
| 9,239,284 B2 | 1/2016 | Livingston |
| 9,239,326 B2 | 1/2016 | Geng et al. |
| 2001/0051717 A1 | 12/2001 | Wakshull et al. |
| 2002/0031786 A1 | 3/2002 | Romaschin et al. |
| 2002/0045195 A1* | 4/2002 | Hubscher ............ G01N 33/558 435/7.9 |
| 2002/0090632 A1 | 7/2002 | Buck, Jr. et al. |
| 2002/0095073 A1 | 7/2002 | Jacobs et al. |
| 2002/0115062 A1 | 8/2002 | Fletcher et al. |
| 2002/0177165 A1 | 11/2002 | Ashkenazi et al. |
| 2003/0017075 A1 | 1/2003 | Angros |
| 2003/0032057 A1 | 2/2003 | Ashkenazi et al. |
| 2003/0032062 A1 | 2/2003 | Ashkenazi et al. |
| 2003/0032063 A1 | 2/2003 | Ashkenazi et al. |
| 2003/0040014 A1 | 2/2003 | Ashkenazi et al. |
| 2003/0044844 A1 | 3/2003 | Ashkenazi et al. |
| 2003/0044902 A1 | 3/2003 | Ashkenazi et al. |
| 2003/0049857 A1 | 3/2003 | Chan |
| 2003/0069178 A1 | 4/2003 | Ashkenazi et al. |
| 2003/0073129 A1 | 4/2003 | Baker et al. |
| 2003/0073149 A1 | 4/2003 | Archer et al. |
| 2003/0077583 A1 | 4/2003 | Ashkenazi et al. |
| 2003/0083248 A1 | 5/2003 | Ashkenazi et al. |
| 2003/0083462 A1 | 5/2003 | Baker et al. |
| 2003/0109420 A1 | 6/2003 | Valkirs et al. |
| 2003/0113718 A1 | 6/2003 | Ashkenazi et al. |
| 2003/0119097 A1 | 6/2003 | Baker et al. |
| 2003/0129186 A1 | 7/2003 | Beliveau et al. |
| 2003/0143652 A1 | 7/2003 | Simonson |
| 2003/0153019 A1 | 8/2003 | Das et al. |
| 2003/0170144 A1 | 9/2003 | Angros |
| 2003/0170721 A1 | 9/2003 | Ashkenazi et al. |
| 2003/0180796 A1 | 9/2003 | Ashkenazi et al. |
| 2003/0180836 A1 | 9/2003 | Baker et al. |
| 2003/0186318 A1 | 10/2003 | Baker et al. |
| 2003/0187192 A1 | 10/2003 | Baker et al. |
| 2003/0191299 A1 | 10/2003 | Baker et al. |
| 2003/0216561 A1 | 11/2003 | Ashkenazi et al. |
| 2003/0220471 A1 | 11/2003 | Baker et al. |
| 2003/0220475 A1 | 11/2003 | Fields et al. |
| 2003/0224452 A1 | 12/2003 | Colgin et al. |

(56) References Cited

U.S. PATENT DOCUMENTS

| | | |
|---|---|---|
| 2003/0224471 A1 | 12/2003 | Jones et al. |
| 2003/0235877 A1 | 12/2003 | Kohl et al. |
| 2004/0006219 A1 | 1/2004 | Ashkenazi et al. |
| 2004/0053342 A1 | 3/2004 | Romaschin et al. |
| 2004/0072241 A1 | 4/2004 | Valkirs et al. |
| 2004/0116350 A1 | 6/2004 | Wentworth, Jr. et al. |
| 2004/0121480 A1 | 6/2004 | Wei et al. |
| 2004/0132106 A1 | 7/2004 | Houthoff et al. |
| 2004/0146516 A1 | 7/2004 | Roben et al. |
| 2004/0157262 A1 | 8/2004 | Kohl et al. |
| 2004/0176270 A1 | 9/2004 | Chen et al. |
| 2004/0214244 A1 | 10/2004 | Tonelli et al. |
| 2004/0229214 A1 | 11/2004 | Fields et al. |
| 2004/0265924 A1 | 12/2004 | Hollyfield et al. |
| 2005/0026823 A1 | 2/2005 | Zankel et al. |
| 2005/0042227 A1 | 2/2005 | Zankel et al. |
| 2005/0053526 A1 | 3/2005 | Angros |
| 2005/0054079 A1 | 3/2005 | Angros |
| 2005/0054080 A1 | 3/2005 | Angros |
| 2005/0085630 A1 | 4/2005 | Olejnik et al. |
| 2005/0096485 A1 | 5/2005 | Scanlan et al. |
| 2005/0112700 A1 | 5/2005 | Perez et al. |
| 2005/0112703 A1 | 5/2005 | Song |
| 2005/0112785 A1 | 5/2005 | Wong et al. |
| 2005/0130207 A1 | 6/2005 | Hainfeld et al. |
| 2005/0130243 A1 | 6/2005 | Zheng et al. |
| 2005/0163774 A1 | 7/2005 | Rosenblum et al. |
| 2005/0170362 A1 | 8/2005 | Wada et al. |
| 2005/0191620 A1 | 9/2005 | McDevitt et al. |
| 2005/0191694 A1 | 9/2005 | Jacobs et al. |
| 2005/0191762 A1 | 9/2005 | Staples et al. |
| 2005/0239116 A1 | 10/2005 | Willey |
| 2005/0255527 A1 | 11/2005 | Yang et al. |
| 2005/0255533 A1 | 11/2005 | Dantini et al. |
| 2005/0272798 A1 | 12/2005 | Ng et al. |
| 2005/0281833 A1 | 12/2005 | Singh et al. |
| 2006/0004081 A1 | 1/2006 | Chen et al. |
| 2006/0013860 A1 | 1/2006 | Ng et al. |
| 2006/0024317 A1 | 2/2006 | Boyd et al. |
| 2006/0029586 A1 | 2/2006 | Chen et al. |
| 2006/0029609 A1 | 2/2006 | Zankel et al. |
| 2006/0035980 A1 | 2/2006 | Scanlan et al. |
| 2006/0040408 A1 | 2/2006 | Jones et al. |
| 2006/0051237 A1 | 3/2006 | Wang et al. |
| 2006/0051824 A1 | 3/2006 | An et al. |
| 2006/0063204 A1 | 3/2006 | Valkirs et al. |
| 2006/0073474 A1 | 4/2006 | Perez et al. |
| 2006/0084184 A1 | 4/2006 | Hu et al. |
| 2006/0160134 A1 | 7/2006 | Melker et al. |
| 2006/0177873 A1 | 8/2006 | Dowd et al. |
| 2006/0194267 A1 | 8/2006 | Vojdani |
| 2006/0204999 A1 | 9/2006 | MacEvicz |
| 2006/0205087 A1 | 9/2006 | Feaster et al. |
| 2006/0217322 A1 | 9/2006 | Bricker et al. |
| 2006/0240453 A1 | 10/2006 | Jacobs et al. |
| 2006/0246526 A1 | 11/2006 | Inganas et al. |
| 2006/0247295 A1 | 11/2006 | Gangwar et al. |
| 2006/0257866 A1 | 11/2006 | Welch et al. |
| 2006/0257941 A1 | 11/2006 | McDevitt et al. |
| 2006/0275841 A1 | 12/2006 | Blankfard et al. |
| 2006/0275846 A1 | 12/2006 | Dorval et al. |
| 2007/0031283 A1 | 2/2007 | Davis et al. |
| 2007/0048746 A1 | 3/2007 | Su et al. |
| 2007/0054317 A1 | 3/2007 | Diebold et al. |
| 2007/0072241 A1 | 3/2007 | Hollyfield et al. |
| 2007/0092517 A1 | 4/2007 | Chang et al. |
| 2007/0099213 A1 | 5/2007 | Pompejus et al. |
| 2007/0104709 A1 | 5/2007 | Li et al. |
| 2007/0141658 A1 | 6/2007 | Chang |
| 2007/0154970 A1 | 7/2007 | Buechler et al. |
| 2007/0167365 A1 | 7/2007 | Beliveau et al. |
| 2007/0184492 A1 | 8/2007 | Wang et al. |
| 2007/0184495 A1 | 8/2007 | Shaari |
| 2007/0196867 A1 | 8/2007 | Mancebo et al. |
| 2007/0231889 A1 | 10/2007 | Angros |
| 2007/0232556 A1 | 10/2007 | Montine et al. |
| 2007/0254285 A1 | 11/2007 | Zhelev et al. |
| 2007/0259376 A1 | 11/2007 | Yoshimura |
| 2007/0269902 A1 | 11/2007 | Beechem et al. |
| 2007/0275427 A1 | 11/2007 | Akimoto et al. |
| 2008/0003626 A1 | 1/2008 | White et al. |
| 2008/0014659 A1 | 1/2008 | Wei et al. |
| 2008/0015465 A1 | 1/2008 | Scuderi |
| 2008/0021196 A1 | 1/2008 | Tang et al. |
| 2008/0032417 A1 | 2/2008 | Olejnik et al. |
| 2008/0064113 A1 | 3/2008 | Goix et al. |
| 2008/0090253 A1 | 4/2008 | Song |
| 2008/0096225 A1 | 4/2008 | Vale et al. |
| 2008/0108101 A1 | 5/2008 | Miyazaki |
| 2008/0112946 A1 | 5/2008 | Koelsch et al. |
| 2008/0118944 A1 | 5/2008 | Larsen et al. |
| 2008/0124747 A1 | 5/2008 | Valkirs et al. |
| 2008/0153092 A1 | 6/2008 | Kienle et al. |
| 2008/0160499 A1 | 7/2008 | Grenier et al. |
| 2008/0160505 A1 | 7/2008 | Hollyfield et al. |
| 2008/0166745 A1 | 7/2008 | Khan et al. |
| 2008/0171352 A1 | 7/2008 | Goix et al. |
| 2008/0181879 A1 | 7/2008 | Catelas et al. |
| 2008/0182262 A1 | 7/2008 | Perez et al. |
| 2008/0199887 A1 | 8/2008 | Valdez et al. |
| 2008/0202933 A1 | 8/2008 | Hu |
| 2008/0248504 A1 | 10/2008 | Ruddell et al. |
| 2008/0254489 A1 | 10/2008 | Perez et al. |
| 2008/0261889 A1 | 10/2008 | Vanmechelen et al. |
| 2008/0262989 A1 | 10/2008 | Su et al. |
| 2008/0279868 A1 | 11/2008 | Boyd et al. |
| 2008/0305559 A1 | 12/2008 | Gonzalez-Sapienza et al. |
| 2008/0311557 A1 | 12/2008 | Elsemore et al. |
| 2008/0311600 A1 | 12/2008 | Elsemore et al. |
| 2008/0318305 A1 | 12/2008 | Angros |
| 2009/0005260 A1 | 1/2009 | Su et al. |
| 2009/0042206 A1 | 2/2009 | Schneider et al. |
| 2009/0061535 A1 | 3/2009 | Dowd et al. |
| 2009/0068635 A1 | 3/2009 | Muerhoff et al. |
| 2009/0068679 A1 | 3/2009 | Vitzthum et al. |
| 2009/0068681 A1 | 3/2009 | Perez et al. |
| 2009/0075881 A1 | 3/2009 | Catelas et al. |
| 2009/0081638 A1 | 3/2009 | Bergwerff et al. |
| 2009/0081699 A1 | 3/2009 | Perez et al. |
| 2009/0093069 A1 | 4/2009 | Valdez et al. |
| 2009/0104170 A1 | 4/2009 | Childs et al. |
| 2009/0105347 A1 | 4/2009 | Scanlan et al. |
| 2009/0111088 A1 | 4/2009 | Martin et al. |
| 2009/0148858 A1 | 6/2009 | Patel et al. |
| 2009/0152114 A1 | 6/2009 | Kawabata et al. |
| 2009/0155850 A1 | 6/2009 | Almagro et al. |
| 2009/0159812 A1 | 6/2009 | Livingston |
| 2009/0175888 A1 | 7/2009 | Ng et al. |
| 2009/0181410 A1 | 7/2009 | Hsieh |
| 2009/0208451 A1 | 8/2009 | Smider et al. |
| 2009/0208960 A1 | 8/2009 | Kelly et al. |
| 2009/0209734 A1 | 8/2009 | Ng et al. |
| 2009/0214554 A1 | 8/2009 | Chang et al. |
| 2009/0220993 A1 | 9/2009 | Turecek et al. |
| 2009/0221100 A1 | 9/2009 | Weber et al. |
| 2009/0221433 A1 | 9/2009 | Barnes et al. |
| 2009/0233319 A1 | 9/2009 | Katagiri et al. |
| 2009/0251683 A1 | 10/2009 | Wardlaw et al. |
| 2009/0270599 A1 | 10/2009 | Angros |
| 2009/0275142 A1 | 11/2009 | Huang et al. |
| 2009/0286227 A1 | 11/2009 | Elsemore et al. |
| 2009/0286228 A1 | 11/2009 | Elsemore et al. |
| 2009/0286229 A1 | 11/2009 | Elsemore et al. |
| 2009/0286230 A1 | 11/2009 | Elsemore et al. |
| 2009/0286231 A1 | 11/2009 | Elsemore et al. |
| 2009/0289182 A1 | 11/2009 | Pevsner |
| 2009/0297438 A1 | 12/2009 | Huang et al. |
| 2009/0305306 A1 | 12/2009 | Stahl et al. |
| 2009/0311260 A1 | 12/2009 | Goddard et al. |
| 2009/0311261 A1 | 12/2009 | Goddard et al. |
| 2009/0314946 A1 | 12/2009 | Song et al. |
| 2009/0325198 A1 | 12/2009 | Holets-McCormack |
| 2009/0325276 A1 | 12/2009 | Battrell et al. |
| 2010/0009429 A1 | 1/2010 | Angros |

(56) References Cited

U.S. PATENT DOCUMENTS

| | | |
|---|---|---|
| 2010/0021457 A1 | 1/2010 | Pfleger et al. |
| 2010/0022029 A1 | 1/2010 | Yoshimura |
| 2010/0034699 A1 | 2/2010 | Chan |
| 2010/0034817 A1 | 2/2010 | Abbas et al. |
| 2010/0035234 A1 | 2/2010 | Donnelly et al. |
| 2010/0035274 A1 | 2/2010 | Murthy et al. |
| 2010/0055033 A1 | 3/2010 | Dimitrov et al. |
| 2010/0068096 A1 | 3/2010 | Angros |
| 2010/0068102 A1 | 3/2010 | Angros |
| 2010/0068135 A1 | 3/2010 | Rock |
| 2010/0092496 A1 | 4/2010 | Boyd et al. |
| 2010/0092999 A1 | 4/2010 | Bricker et al. |
| 2010/0098684 A1 | 4/2010 | Scuderi et al. |
| 2010/0113476 A1 | 5/2010 | Chen et al. |
| 2010/0130402 A1 | 5/2010 | Pfuetzner et al. |
| 2010/0144543 A1 | 6/2010 | Witcher et al. |
| 2010/0151500 A1 | 6/2010 | Geng et al. |
| 2010/0173797 A1 | 7/2010 | Jacobs et al. |
| 2010/0183581 A1 | 7/2010 | Beliveau et al. |
| 2010/0184087 A1 | 7/2010 | Kosmeder et al. |
| 2010/0196207 A1 | 8/2010 | Steinmiller et al. |
| 2010/0221272 A1 | 9/2010 | Napper et al. |
| 2010/0221750 A1 | 9/2010 | Perez et al. |
| 2010/0233741 A1 | 9/2010 | Wang et al. |
| 2010/0235930 A1 | 9/2010 | Shaw et al. |
| 2010/0247571 A1* | 9/2010 | Wong ............... A61K 39/145 424/208.1 |
| 2010/0248217 A1 | 9/2010 | Elsemore et al. |
| 2010/0248273 A1 | 9/2010 | Campbell et al. |
| 2010/0279432 A1 | 11/2010 | Muerhoff et al. |
| 2010/0323343 A1* | 12/2010 | Egan ................ C12Q 1/6804 435/5 |
| 2010/0323369 A1 | 12/2010 | Marlborough et al. |
| 2010/0329929 A1 | 12/2010 | Goix et al. |
| 2010/0330591 A1 | 12/2010 | Mancebo et al. |
| 2011/0020839 A1 | 1/2011 | Perez et al. |
| 2011/0039278 A1 | 2/2011 | Pieribone |
| 2011/0053161 A1 | 3/2011 | Hong et al. |
| 2011/0053171 A1 | 3/2011 | Gerdes et al. |
| 2011/0065127 A1 | 3/2011 | Heller et al. |
| 2011/0076268 A1 | 3/2011 | Williamson et al. |
| 2011/0076701 A1 | 3/2011 | Dodds |
| 2011/0086340 A1 | 4/2011 | Elsemore et al. |
| 2011/0097735 A1 | 4/2011 | Mao et al. |
| 2011/0111415 A1 | 5/2011 | Dodds |
| 2011/0111425 A1 | 5/2011 | Rylatt et al. |
| 2011/0130306 A1 | 6/2011 | Chang |
| 2011/0136099 A1 | 6/2011 | Schneider et al. |
| 2011/0137851 A1 | 6/2011 | Cavet et al. |
| 2011/0142763 A1 | 6/2011 | Zankel et al. |
| 2011/0143351 A1 | 6/2011 | Rudd et al. |
| 2011/0171662 A1 | 7/2011 | Grenier et al. |
| 2011/0177529 A1 | 7/2011 | Shaari |
| 2011/0177534 A1 | 7/2011 | Salant et al. |
| 2011/0184747 A1 | 7/2011 | Bozic et al. |
| 2011/0189084 A1 | 8/2011 | Zankel |
| 2011/0189166 A1 | 8/2011 | Boucher |
| 2011/0201018 A1 | 8/2011 | Perez et al. |
| 2011/0207149 A1 | 8/2011 | Perez et al. |
| 2011/0223683 A1 | 9/2011 | Regnier et al. |
| 2011/0229905 A1 | 9/2011 | Kimchi et al. |
| 2011/0245090 A1 | 10/2011 | Abbas et al. |
| 2011/0250614 A1 | 10/2011 | Perez et al. |
| 2011/0263043 A1 | 10/2011 | Livingston |
| 2011/0269159 A1 | 11/2011 | Campbell et al. |
| 2011/0269634 A1 | 11/2011 | Perez et al. |
| 2011/0294140 A1 | 12/2011 | Holets-McCormack |
| 2011/0294200 A1 | 12/2011 | Wardlaw et al. |
| 2011/0311522 A1* | 12/2011 | Chen ................ C07K 16/1018 424/133.1 |
| 2011/0312085 A1 | 12/2011 | Angros |
| 2011/0312531 A1 | 12/2011 | Jacobs et al. |
| 2011/0318825 A1 | 12/2011 | Angros |
| 2012/0009666 A1 | 1/2012 | Gerdes et al. |
| 2012/0015376 A1 | 1/2012 | Bornhop |
| 2012/0028280 A1 | 2/2012 | Bricker et al. |
| 2012/0034160 A1 | 2/2012 | Ghayur et al. |
| 2012/0058570 A1 | 3/2012 | Angros |
| 2012/0065095 A1 | 3/2012 | Kienle et al. |
| 2012/0070849 A1 | 3/2012 | Perez et al. |
| 2012/0073969 A1 | 3/2012 | Campbell et al. |
| 2012/0087831 A1 | 4/2012 | Chan |
| 2012/0087858 A1 | 4/2012 | Ghayur et al. |
| 2012/0088689 A1 | 4/2012 | Mayer et al. |
| 2012/0107198 A1 | 5/2012 | Angros |
| 2012/0122129 A1 | 5/2012 | Shaari |
| 2012/0125788 A1 | 5/2012 | Diebold et al. |
| 2012/0129190 A1 | 5/2012 | Chiu et al. |
| 2012/0156693 A1 | 6/2012 | Wong et al. |
| 2012/0203465 A1 | 8/2012 | Callewaert et al. |
| 2012/0208983 A1 | 8/2012 | Elsemore et al. |
| 2012/0225438 A1 | 9/2012 | Passavant et al. |
| 2012/0237401 A1 | 9/2012 | Steinmiller et al. |
| 2012/0276548 A1 | 11/2012 | Schmidt |
| 2012/0301896 A1 | 11/2012 | Wang et al. |
| 2012/0301905 A1 | 11/2012 | Wang et al. |
| 2012/0301906 A1 | 11/2012 | Collier et al. |
| 2012/0309026 A1 | 12/2012 | Perez et al. |
| 2012/0329176 A1 | 12/2012 | Muerhoff et al. |
| 2013/0040286 A1 | 2/2013 | Chan |
| 2013/0052748 A1 | 2/2013 | Campbell et al. |
| 2013/0059400 A1 | 3/2013 | Livingston |
| 2013/0065324 A1 | 3/2013 | Mitchell et al. |
| 2013/0084585 A1 | 4/2013 | Stridsberg et al. |
| 2013/0122518 A1 | 5/2013 | Callewaert et al. |
| 2013/0130285 A1 | 5/2013 | Atkinson et al. |
| 2013/0130366 A1 | 5/2013 | Angros |
| 2013/0137598 A1 | 5/2013 | Verschoor et al. |
| 2013/0137607 A1 | 5/2013 | Ghatak |
| 2013/0137632 A1 | 5/2013 | Pfuetzner et al. |
| 2013/0137748 A1 | 5/2013 | Hamamoto et al. |
| 2013/0149694 A1 | 6/2013 | Elsemore et al. |
| 2013/0153420 A1 | 6/2013 | Hu |
| 2013/0157295 A1 | 6/2013 | Bricker et al. |
| 2013/0157381 A1 | 6/2013 | Pang et al. |
| 2013/0164739 A1 | 6/2013 | Heemstra |
| 2013/0165332 A1 | 6/2013 | Abbas et al. |
| 2013/0177970 A1 | 7/2013 | Perez et al. |
| 2013/0184188 A1 | 7/2013 | Ewart et al. |
| 2013/0189797 A1 | 7/2013 | Quinn |
| 2013/0210669 A1 | 8/2013 | Pieribone |
| 2013/0213822 A1 | 8/2013 | Diebold et al. |
| 2013/0217146 A1 | 8/2013 | Wardlaw et al. |
| 2013/0224759 A1 | 8/2013 | Elsemore et al. |
| 2013/0230844 A1 | 9/2013 | Egan et al. |
| 2013/0252245 A1 | 9/2013 | Micallef et al. |
| 2013/0252321 A1 | 9/2013 | Steinmiller et al. |
| 2013/0261023 A1 | 10/2013 | Barnes et al. |
| 2013/0267010 A1 | 10/2013 | Wang et al. |
| 2013/0273576 A1 | 10/2013 | Campbell et al. |
| 2013/0280738 A1 | 10/2013 | Salant et al. |
| 2013/0280740 A1 | 10/2013 | Yerramilli et al. |
| 2013/0281660 A1 | 10/2013 | Heller et al. |
| 2013/0284942 A1 | 10/2013 | Livingston |
| 2013/0288347 A1 | 10/2013 | Livingston |
| 2013/0288388 A1 | 10/2013 | Freeby et al. |
| 2013/0309661 A1 | 11/2013 | Bomhop |
| 2013/0344508 A1 | 12/2013 | Schwartz et al. |
| 2014/0004506 A1 | 1/2014 | Song |
| 2014/0024024 A1 | 1/2014 | Sood et al. |
| 2014/0024057 A1 | 1/2014 | Passavant et al. |
| 2014/0065722 A1 | 3/2014 | Goix et al. |
| 2014/0072989 A1 | 3/2014 | Collier et al. |
| 2014/0093893 A1 | 4/2014 | Angros |
| 2014/0170068 A1 | 6/2014 | Thiele et al. |
| 2014/0170682 A1 | 6/2014 | Pevsner |
| 2014/0170684 A1 | 6/2014 | Elsemore et al. |
| 2014/0178899 A1 | 6/2014 | Kimchi et al. |
| 2014/0178904 A1 | 6/2014 | Zimring |
| 2014/0186934 A1 | 7/2014 | Chan |
| 2014/0193332 A1 | 7/2014 | Goddard et al. |
| 2014/0205994 A1 | 7/2014 | Elsemore et al. |
| 2014/0206020 A1 | 7/2014 | Valdez et al. |
| 2014/0219912 A1 | 8/2014 | Ghayur et al. |

(56) References Cited

U.S. PATENT DOCUMENTS

| | | |
|---|---|---|
| 2014/0220019 A1 | 8/2014 | Ghayur et al. |
| 2014/0227714 A1 | 8/2014 | Angros |
| 2014/0234208 A1 | 8/2014 | Ghayur et al. |
| 2014/0234340 A1 | 8/2014 | Igawa et al. |
| 2014/0242720 A1 | 8/2014 | Nishida et al. |
| 2014/0242723 A1 | 8/2014 | Yerramilli et al. |
| 2014/0249043 A1 | 9/2014 | Schneider et al. |
| 2014/0287431 A1 | 9/2014 | Hibino et al. |
| 2014/0294850 A1 | 10/2014 | Ronco et al. |
| 2014/0302509 A1 | 10/2014 | Moerman et al. |
| 2014/0303023 A1 | 10/2014 | Mayer et al. |
| 2014/0303033 A1 | 10/2014 | Ehricht et al. |
| 2014/0308168 A1 | 10/2014 | Steinmiller et al. |
| 2014/0323336 A1 | 10/2014 | Kosmeder, II et al. |
| 2014/0323347 A1 | 10/2014 | Ghatak |
| 2014/0323545 A1 | 10/2014 | Garcia |
| 2014/0329705 A1 | 11/2014 | Wong et al. |
| 2014/0342380 A1 | 11/2014 | Saal |
| 2014/0349318 A1 | 11/2014 | Pevsner |
| 2014/0360878 A1 | 12/2014 | Paulus et al. |
| 2014/0371086 A1 | 12/2014 | Abbas et al. |
| 2015/0011018 A1 | 1/2015 | Pieribone |
| 2015/0024456 A1 | 1/2015 | Valdez et al. |
| 2015/0030504 A1 | 1/2015 | Pang et al. |
| 2015/0031581 A1 | 1/2015 | Kema et al. |
| 2015/0056687 A1* | 2/2015 | Tyrrell .................. B01L 3/5023 435/287.2 |
| 2015/0072352 A1 | 3/2015 | Heemstra |
| 2015/0072359 A1 | 3/2015 | Stubenrauch et al. |
| 2015/0094449 A1 | 4/2015 | Heller et al. |
| 2015/0099650 A1 | 4/2015 | Sood et al. |
| 2015/0105280 A1 | 4/2015 | Regnier et al. |
| 2015/0108367 A1 | 4/2015 | Livingston |
| 2015/0140001 A1 | 5/2015 | Lee et al. |
| 2015/0160217 A1 | 6/2015 | Wong et al. |
| 2015/0169840 A1 | 6/2015 | Kupfer et al. |
| 2015/0192576 A1 | 7/2015 | Manez Mendiluce |
| 2015/0196908 A9 | 7/2015 | Steinmiller et al. |
| 2015/0219635 A1 | 8/2015 | Lawson et al. |
| 2015/0219639 A1 | 8/2015 | Pfuetzner et al. |
| 2015/0226732 A1 | 8/2015 | De Theije et al. |
| 2015/0241442 A1 | 8/2015 | Nolan et al. |
| 2015/0260718 A1 | 9/2015 | Elsemore et al. |
| 2015/0276732 A1 | 10/2015 | Campbell et al. |
| 2015/0299308 A1 | 10/2015 | Vitzthum et al. |
| 2015/0301050 A1 | 10/2015 | Wang et al. |
| 2015/0301058 A1 | 10/2015 | Schettini et al. |
| 2015/0338396 A1 | 11/2015 | Narimatsu et al. |
| 2015/0355172 A1 | 12/2015 | Kraus et al. |
| 2015/0369815 A1 | 12/2015 | Micallef et al. |
| 2015/0377909 A1 | 12/2015 | Cavet et al. |

FOREIGN PATENT DOCUMENTS

| | | |
|---|---|---|
| EP | 0122059 A2 | 10/1984 |
| EP | 0125118 A2 | 11/1984 |
| EP | 0160467 A2 | 11/1985 |
| EP | 0199261 A2 | 10/1986 |
| EP | 0212670 A2 | 3/1987 |
| EP | 0231010 A2 | 8/1987 |
| EP | 0475783 A1 | 3/1992 |
| EP | 1847610 A2 | 10/2007 |
| EP | 1947183 A1 | 7/2008 |
| EP | 1961293 A2 | 8/2008 |
| EP | 1980573 A2 | 10/2008 |
| EP | 1985630 A2 | 10/2008 |
| EP | 2003451 A2 | 12/2008 |
| EP | 2020239 A1 | 2/2009 |
| EP | 2052742 A1 | 4/2009 |
| EP | 2113566 A1 | 11/2009 |
| EP | 2153848 A2 | 2/2010 |
| EP | 2172478 A2 | 4/2010 |
| EP | 2258726 A1 | 12/2010 |
| EP | 2261256 A2 | 12/2010 |
| EP | 2266986 A1 | 12/2010 |
| EP | 2275447 A1 | 1/2011 |
| EP | 2293067 A2 | 3/2011 |
| EP | 2298802 A1 | 3/2011 |
| EP | 2316974 A1 | 5/2011 |
| EP | 2327985 A2 | 6/2011 |
| EP | 2333113 A1 | 6/2011 |
| EP | 2354163 A2 | 8/2011 |
| EP | 2381256 A1 | 10/2011 |
| EP | 2389943 A1 | 11/2011 |
| EP | 2399586 A1 | 12/2011 |
| EP | 2416157 A2 | 2/2012 |
| EP | 2423201 A1 | 2/2012 |
| EP | 2436774 A2 | 4/2012 |
| EP | 2453024 A2 | 5/2012 |
| EP | 2479578 A1 | 7/2012 |
| EP | 2511266 A1 | 10/2012 |
| EP | 2564864 A2 | 3/2013 |
| EP | 2605015 A1 | 6/2013 |
| EP | 2712620 A1 | 4/2014 |
| EP | 2757091 A1 | 7/2014 |
| EP | 2902036 A1 | 8/2015 |
| EP | 2942357 A1 | 11/2015 |
| GB | 2204398 A | 11/1988 |
| WO | WO8402193 A1 | 6/1984 |
| WO | WO8908258 A1 | 9/1989 |
| WO | WO9001564 A1 | 2/1990 |
| WO | WO9106007 A1 | 5/1991 |
| WO | WO9108480 A1 | 6/1991 |
| WO | WO9306487 A1 | 4/1993 |
| WO | WO9401768 A1 | 1/1994 |
| WO | WO9532414 A1 | 11/1995 |
| WO | WO9804743 A1 | 2/1998 |
| WO | WO0125788 A1 | 4/2001 |
| WO | WO03057179 A2 | 7/2003 |
| WO | WO03065002 A2 | 8/2003 |
| WO | WO2005002515 A2 | 1/2005 |
| WO | WO2005077093 A2 | 8/2005 |
| WO | WO2007035716 A2 | 3/2007 |
| WO | WO2007038658 A2 | 4/2007 |
| WO | WO2007056352 A2 | 5/2007 |
| WO | WO2008020293 A2 | 2/2008 |
| WO | WO2008118324 A2 | 10/2008 |
| WO | WO2010065867 A1 | 6/2010 |
| WO | WO2011020079 A1 | 2/2011 |
| WO | WO2011035205 A2 | 3/2011 |
| WO | WO2011056997 A1 | 5/2011 |
| WO | WO2011094536 A1 | 8/2011 |
| WO | WO2011156759 A1 | 12/2011 |
| WO | WO2012006596 A2 | 1/2012 |
| WO | WO2012012718 A2 | 1/2012 |
| WO | WO2012092323 A1 | 7/2012 |
| WO | WO2012099897 A1 | 7/2012 |
| WO | WO2012149047 A1 | 11/2012 |
| WO | WO2013007839 A1 | 1/2013 |
| WO | WO2013022738 A1 | 2/2013 |
| WO | WO2013111054 A1 | 8/2013 |
| WO | WO2014012077 A1 | 1/2014 |
| WO | WO2014015076 A1 | 1/2014 |
| WO | WO2015038978 A1 | 3/2015 |

* cited by examiner

| | Positive Test | Negative Test | Invalid Test | Invalid Test |
|---|---|---|---|---|
| Strip Assay Test | | | | |
| Control Band | + | + | - | - |
| Test Band | + | - | - | - |

Fig. 2A

Fig. 2B

EKEGSYPKLKNSggg DYKDDDDK ggg AGPR↓SLX ggg HHHHHH

[SEQ ID NO: 008]

EKKGSYPKLKNSggg DYKDDDDK ggg AGPR↓SLX ggg HHHHHH

[SEQ ID NO: 009]

| Test | Patient 1 | Patient 2 | Patient 3 |
|---|---|---|---|
| | Positive/ Positive E1/ E2 | Positive/ Negative E1/ E2 | Negative/ Positive E1/ E2 |
| Strip Assay Test | — — <br> — — | — — <br> — | — — <br> — |
| Control Band | + + | + + | + + |
| Test Band | + + | + − | − + |

Fig. 4

Only positive control tests shown

COMPOSITIONS AND METHODS FOR DETERMINING SUCCESSFUL IMMUNIZATION BY ONE OR MORE VACCINES

CROSS REFERENCE TO RELATED APPLICATIONS

This application is a Division of U.S. patent application Ser. No. 13/209,573, filed Aug. 15, 2011, now U.S. Pat. No. 8,956,859, issued Feb. 17, 2015, which is a non-provisional of, and claims benefit of priority from, U.S. Provisional Patent Application Ser. No. 61/373,375, filed Aug. 13, 2010, the entirety of which are expressly incorporated herein by reference.

1. FIELD OF THE INVENTION

This invention is related to the field of diagnostic methods and kits relating to immune responses of a host, including humans.

2. BACKGROUND OF THE INVENTION

Citation or identification of any reference herein, or any section of this application shall not be construed as an admission that such reference is available as prior art to the present application. The disclosures of each of these publications are hereby incorporated by reference in their entirety in this application, and shall be treated as if the entirety thereof forms a part of this application.

In the United States, conventional influenza types A or B viral epidemics can cause illness in 10% to 20% of people and are associated with an average of 36,000 deaths and an estimated 120,000-200,000 hospitalizations per year (estimates vary to do complications of pneumonia). In the advent of a highly pathogenic avian type influenza pandemic, the potential for severe morbidity and mortality will be substantially higher, and will occur during a time where the healthcare system is overburden. Many people will receive prior vaccination. During conventional epidemics, those receiving a vaccine do so with the presumption that 1) the vaccination will be successful and 2) that the vaccine matches the emerging pathogenic strain. Prior to, and during, a pandemic of highly pathogenic avian influenza or other influenza strain, those two assumptions may be inaccurate, yet, at the present time, there is no readily available means for people to determine if these immunization criteria have been met.

Currently established serological methods for detection of antibodies to influenza are necessary to conduct clinical trials of influenza vaccination, but are technical in nature, not accessible to the general public, and do not compare results for different antigens that would allow determination of which vaccine may have been successful when one or more vaccines has been administered (Cheng et al., 2008, Serologic and genetic characterization analysis of a highly pathogenic influenza virus (H5N1) isolated from an infected man in Shenzhen, J. Med. Virol. 80: 1058-1064; Katz et al., 1999, Antibody response in individuals infected with avian influenza A (H5N1) virus and detection of anti-H5 antibody among household and social contacts. J. Infect. Dis. 180: 1763-1770; Rowe et al., 1999, detection of antibody to avian influenza A (H5N1) virus in human serum using a combination of serologic assays, J. Clin. Microbiol. 37: 937-943). Such methods determine the immune response, or seroconversion, in the host, which are specific antibody responses to vaccination or post viral infection, and should not be confused with diagnostics that determine the presence of the physical virus particle during infection such as described by Zambon and Ellis, 2001 (Molecular methods for diagnosis of influenza International Congress Series 1219: 267-273).

Following influenza vaccination performed in mid-1997 a study was performed by de Jong et al., (2001, Antibody responses in elderly to influenza vaccination in case of an antigenic mismatch, International Congress Series 1219: 707-711) wherein sera were obtained from vaccinees of various ages, including residents of nursing homes over 60 years of age. As a surrogate marker for induction of protection by influenza vaccination, they studied the haemagglutination inhibition (HI) antibody response of the vaccinees to vaccine and epidemic strains of the three (sub)types A(H3N2), A(H1N1), and B. Statistical methods included the paired t-test, the McNemar c2-test, the one-way ANOVA, the Pearson c2-test, and a "minimum-maximum" analysis, newly developed by Dr G. Lüchters from Bonn. In accordance with usual practice, the "50% protective threshold" of HI antibodies was set at 1:40 (Periera et al., 1972, Prevalence of antibody to current influenza viruses and effect of vaccination on antibody response. British Medical Journal 4:701-703).

In the influenza season of 1997/1998, a major antigenic mismatch of the H3N2 vaccine component occurred. They found that the vigor of immune responses declined at higher ages. Sera from influenza vaccinees was further used to assess the magnitude of this effect in case of an antigenic mismatch. At advanced age, the homologous antibody response was lowered, starting above 60 years. In addition, they found that the cross-reactivity of the formed antibodies to the drifted field virus decreased with age, starting above 70 years. They concluded that effect of ageing on the induction of "protective" titres ($\geq 40$) of HI antibodies against an emerging deviant strain can be severe, and that in the 1997/1998 season, in those above 80 years of age, the percentage of vaccinees acquiring such titres against the major epidemic H3N2 virus was only about 15%.

In the study by Keren et al., 2005 (Failure of influenza vaccination in the aged, J. Med. Virol. 25: 85-89), they found that in a cohort of 127 nursing home residents aged 60-98 years vaccinated during the winter of 1985-86 with the A-Chile 1/83 (c), A-Philippines 2/82 (p), and B-USSR (B) commercial influenza vaccines, that before vaccination 40%, 23%, and 69% were susceptible to influenza Ac, Ap, and B, respectively [hemagglutinin inhibition (H.I.) titer <1:40] and that one month following initial vaccination, 32 patients [25%] remained unprotected against two or all three vaccine strains. The unprotected patients were revaccinated with the same influenza vaccine and followed up. At five months 11%, 19%, and 23% of the initial cohort were still unprotected against Ac, Ap, and B strains, respectively. They conclude that two conventional influenza vaccines administered one month apart leave unprotected 30% of healthy elderly people who are initial influenza vaccine failures.

Physicians have long believed that the elderly often fail to generate a sufficient immune response for protection when given a standard seasonal flu shot, as illustrated in the studies by de Jong et al., 2001 and Keren et al., 2005 described above. About 90 percent of the estimated 36,000 people who die from flu-related causes in the United States each year are 65 and older, and account for an estimated 120,000 hospitalizations. Although fewer children die from influenza, infection results in an additional 20,000 hospitalizations per year, with a total up to 200,000 resulting from all influenza infections. Unfortunately, of those who are vaccinated with conventional vaccines, there is no convention regarding determination of the extent to which the vaccination was successful. The fact that the vaccine may not be antigenically matched to the emergent seasonal vaccine further compromises the overall protective effect on the population. Despite the obvious "leap-of-faith" in being vaccinated without determining effectiveness, there has been no apparent movement toward developing a diagnostic test that would inform a patient whether they were adequately protected.

Highly pathogenic H5N1 avian influenza presents a number of similar complications as conventional influenza as well as new challenges in effectively protecting individuals within a population. First, the vaccines for H5N1 have not been subjected to an epidemiological challenge for effectiveness (i.e., an actual pandemic); surrogate markers such as the level of anti-influenza antibodies are used to gauge effectiveness. It is generally accepted that an antibody level of 1:40 (higher numbers indicate better protection) is required to give 50% protection for a standard influenza. A number of vaccine makers have increased production of conventional-type vaccine for H5N1, and a number of biotechnology companies have introduced new approaches to generating novel vaccines and have shown the ability to generate anti-H5N1 antibodies, including the use of virus-like particles (Pusko et al., 2010, Recombinant H1N1 virus-like particle vaccine elicits protective immunity in ferrets against the 2009 pandemic H1N1 influenza virus, *Vaccine*, 28:4771-4776) or influenza proteins produced in tobacco plants (Lico et al., 2009, Plant-produced potato virus X chimeric particles displaying an influenza virus-derived peptide activate specific CD8+ T cells in mice. *Vaccine*, 27:5069-76). However, given the highly pathogenic nature of the H5N1 avian influenza (50-80% mortality), an antibody level of 40 may not be effective at all, at least on its own. Thus, a remarkably novel situation exists in terms of the number of different vaccine manufacturers and types of vaccines that may be available for H5N1 for which the ramifications have not been explored. This situation will also be complicated by differences in the antigens used to prepare the vaccine and their match to the emerging pathogen or pathogens. In countries where multiple types of vaccines are available, it seems probable that people will question the efficacy of individual vaccine types, which would require diagnostic testing in order to determine; a situation that has not been previously recognized and for which no solution has been proposed. The potential ineffectiveness of a single vaccine may lead many to seek a second vaccination using the same or an alternative vaccine type. While it would seem desirable to proceed to multiple vaccinations without testing, only through testing will the individuals within the population know if and/or when a vaccine or set of vaccines has been effective for them personally and will the medical field know which vaccines and/or combination of vaccines are effective within a population. The consequence of an unsuccessful vaccination and infection by H5N1 may be death, dramatically skewing the cost-benefit ratio analysis. Furthermore, in the advent of a shortage, the availability of a second vaccine for those already receiving an initial injection may not be justifiable without a diagnostic test indicating its necessity, even if the test were more expensive than the vaccine itself.

3. SUMMARY OF THE INVENTION

The present invention uses novel methods and provides a diagnostic kit for determining successful vaccination for influenza and other infectious diseases. Unlike conventional diagnosis of successful vaccination, the present invention provides simultaneous testing against multiple antigens containing "fingerprint" signatures that allows not only the determination of successful vaccination, but the ability to determine which vaccine was successful in the event multiple vaccines are administered to the same host. The diagnostic influenza vaccination test also provides information as to the strain(s) of influenza for which vaccination has been successful, as well as subtypes, immune escape variants, and neurominadase resistant strains. The diagnostic device and/or kit are particularly useful for highly pathogenic influenza, such as the H1N1 "swine" and H5N1 "avian" flu strains.

OBJECTS OF THE INVENTION

Influenza and vaccines for the prevention of influenza and the associated immune responses are used as a non-limiting illustrative example. The present invention comprises an in vitro diagnostic test that can be informative of the following:
1) Presence and semi-quantitative concentration of anti-influenza antibodies (i.e., successful immunization) to different influenza antigens.
2) Strain of influenza to which the antibodies belong, including conventional H1N1 and highly pathogenic H5N1 viruses and emergent subtypes. The complete set of subtypes for influenza A could include the 16 different hemagglutinin subtypes H1, H2, H3, H4, H6, H7, H8, H9 H10 H11, H12, H13, H14, H15 or H16 or 9 different neuraminidase subtypes N1 N2 N3 N4 N5 N6 N7 N8 or N9. The diagnostic proteins may also include one or more nucleoprotein (NP), M1, M2, NS1, NS2 (NEP), PA, PB1, PB1-F2 and/or PB2 which may or may not be present in certain vaccine preparations.
3) Type of vaccine that generated the immune response (where applicable in patients receiving more than one type of vaccine). The information may include specific characteristics including immune escape variants, or oseltamivir-resistant mutants (e.g., the H274Y mutation in the neurominidase or other compensatory mutations; Bloom et al., Permissive secondary mutations enable the evolution of influenza oseltamivir resistance, Science 328: 1272-1275).
4) Under some circumstances, such as when one or more vaccine preparations do not have the entire protein content of the virus, such as being limited to the hemagglutinin and/or neurominadase, the test can determine the difference between infection by the wild-type virus or vaccination by one or more vaccines.

It is therefore an object to provide a system and method for testing for presence of an antibodies to an antigen from a host, comprising providing: a reactant layer, into which are absorbed the antigen, an anti-host immunoglobulin IgM antibody bound to a ligand, and a detector comprising a non-host anti-antigen IgG antibody conjugated to colloidal particles; a test strip, in fluid communication with the reactant layer at a portion thereof, to which is immobilized a ligand binding agent at a test area and anti-non-host IgG immobilized at a control area, the test area being spaced more proximate to the reactant layer than the control area; and a sample well.

A serum specimen from a host is placed in the sample well, and host antigen-specific antibodies in the specimen are permitted to selectively form a quaternary complex with the detector/antigen/IgM complex. The quaternary complex migrates through the test strip and is captured at the test area by the immobilized ligand binding agent. Detector/antigen/ IgM complex unbound to antigen-specific host antibodies migrate through the test strip, past the test area, and are captured at the control area by the immobilized anti-IgG. A presence of the host antigen-specific antibodies is detected by an indication at the test area and validity of the test is ensured by an indication at the control area. The colloidal particles are preferably readily detectable, though other types of detectors may also be used in substitution for the colloidal particles.

It is a further object to provide a testing system and method for presence of an antibodies to a particular antigen from a host, comprising: providing a reactant layer, having a the particular antigen, an anti-host immunoglobulin IgM antibody bound to a ligand, and a non-host anti-antigen IgG antibody conjugated to a detector; forming a complex by adding serum containing host antibodies to the particular antigen, wherein the host antibodies and the IgG bind the particular antigen, and the IgM binds the host antibodies; migrating the complex on a strip toward a first region having an immobilized ligand binding agent which binds and ceases migration of the IgM antibody and any complexes including the IgM antibody; migrating residual of the complex past the first region to a second region having immobilized anti-non-host IgG immobilized at a control area, which binds the non-host IgG antibody and any complexes including the non-host IgG antibody, wherein, if the host antibodies have a high affinity for the antigen and are present in sufficient quantity, a complex comprising the antigen, the host antibodies, and the anti-host IgM antibodies and the non-host anti-antigen IgG and detector are retained in the first region for detection based on the presence of the detector, and if the host antibodies have a low affinity for the antigen or are not present in sufficient quantity, a complex comprising the antigen, the non-host anti-antigen IgG and detector, will migrate past the first region and b retained at the second region for detection based on the presence of the detector.

The ligand is preferably biotin and the ligand binding agent is preferably strepavidin.

The colloidal particles are preferably gold particles.

The concentrations of antigen, anti-host immunoglobulin IgM antibody bound to the ligand, the detector, immobilized ligand binding agent and immobilized anti-IgG are provided, based on calibration with pooled sera from successfully immunized hosts, to produce a positive indication at an IgM Index value of at least 1.1 of an IgM Capture ELISA device and a negative indication results below an IgM Index value of 1.1.

The antigen is, for example, an influenza hemagglutinin (e.g., hemagglutinin or neuraminidase), which may be produced by a bacterium. The antigen may comprise a gene product of an inserted gene in a genetically engineered bacterium. The antigen may be an influenza hemagglutinin produced by a genetically engineered bacterium, a non-glycosylated protein produced by a bacteria corresponding to a glycosylated protein produced by a virus during mammalian infection, produced in insect cells, a glycosylated antigen produced in an insect cell/baculovirus method, produced in an insect cell and has (or is absent) a hexahistidine tag, correspond to an influenza hemagglutinin antigen if an influenza strain which causes human disease, correspond to an influenza neuraminidase antigen of an influenza strain which causes human disease, an epitope peptide of a pathogenic influenza, and/or the epitope peptide may comprise an epitope hemagglutinin peptide modified to be covalently bound to a non-hemaggutinin epitope peptide.

The anti-host immunoglobulin IgM antibody bound to a ligand may comprise biotinylated goat-antihuman IgM.

The non-host anti-antigen IgG antibody may comprise mouse monoclonal IgG anti-antigen antibody.

The anti-IgG immobilized at the control area may comprise rabbit antimouse IgG-Fc. The mouse monoclonal IgG anti-antigen antibody may be conjugated onto colloidal gold particles.

The antigen, the anti-host immunoglobulin IgM antibody bound to a ligand, and the detector may be dispensed as at least one solution on the reactant layer and subsequently lyophilized.

The reactant layer may comprise a polyester pad. The test strip may comprise a nitrocellulose membrane. The test strip may comprise an elongated strip, on which the reactant layer is situated on one side, and the test area and control area are sequentially disposed distant from the test strip. The sample well may be provided on top of the reactant layer, and between the reactant layer and the test strip is disposed at least one flow control layer. The test system may further comprise an absorbent pad in fluid communication with the test strip disposed on an opposite side of the control area from the reactant layer, wherein the absorbent pad induces a bulk fluid flow from the reactant layer to the absorbent pad.

The method may further comprise vaccinating the host with the antigen, and/or vaccinating the host with multiple antigens concurrently.

The test may further comprise a plurality of control areas, each associated with response indicative of absence of antibodies to a different antigen, wherein for each different antigen, a corresponding anti-non-host IgG antibody having respectively different conserved portions, conjugated to colloidal particles is provided, and at each respective control area, a corresponding anti-non-host IgG specific for the respectively different conserved portions is immobilized.

4. BRIEF DESCRIPTION OF THE DRAWINGS

FIG. 1A shows an arrangement of different components in a strip test design and examples of positive (both bands present), negative (test band absent), and invalid (no control band) test results.

FIG. 1B shows tabular results of the test strip, in which positive test results are suggestive of influenza immunity as the IgM levels are at or above the established cut-off level, and invalid results indicate that the test must be repeated. rFLU, recombinant influenza antigen; Mab, monoclonal antibody.

FIGS. 2A and 2B shows a determination of an epitope region of a sequence based on known epitopic regions.

FIGS. 3A, 3B and 3C show a modification of an epitope for use in a strip assay determining the response to one or more epitopes.

FIG. 4 shows the tabular results of a test strip with two representative set of finger print peptide sequences for two epitopes (E1 and E2) of H1 hemagglutinins, where the first epitope is described in FIG. 3B and the second epitope is described in FIG. 3C.

5. DETAILED DESCRIPTION OF THE INVENTION

The present invention provides, according to various embodiments, compositions and methods for diagnosis of successful vaccination that can determine infectious subtypes for which an individual is vaccinated, and provides a means to distinguish between immune responses in vaccinees that have received more than one type of vaccine. The types of infectious diseases may generally include prions, viruses, bacteria, protozoans (protists), fungi and helminthes (Mandell, Bennett and Dolin 2010, Principles and Practices of Infectious Diseases, 7$^{th}$ Edition, Elsiever Publishers, 4320 pages). A particularly useful application is for assessment of influenza vaccination.

For reasons of clarity, the detailed description is divided into the following subsections: 1) infectious types and subtypes, 2) antigens, 3) epitopes, 4) posttranslational modifications of antigens and epitopes, and 5) antibody-based tests.

5.1. Infectious Types and Subtypes.

There are three types of influenza viruses Influenza A, B, and C. Influenza type A viruses are divided into subtypes based on two proteins on the surface of the virus. These proteins are termed hemagglutinin (H) and neuraminidase (N). Influenza A viruses are divided into subtypes based on these two proteins. There are 16 different hemagglutinin subtypes H1, H2, H3, H4, H6, H7, H8, H9 H10 H11 H12, H13, H14, H15 or H16 and 9 different neuraminidase subtypes N1 N2 N3 N4 N5 N6 N7 N8 or N9, all of which have been found among influenza A viruses in wild birds. Wild birds are the primary natural reservoir for all subtypes of influenza A viruses and are thought to be the source of influenza A viruses in all other animals, such as pigs, giving rise to "swine flu" strains. The current subtypes of influenza A viruses found in people are A(H1N1) and A(H3N2). Influenza B virus is not divided into subtypes. Influenza A genome contains 11 genes on eight pieces of RNA, encoding for 11 proteins; hemagglutinin, neuraminidase (NA), nucleoprotein (NP), M1, M2, NS1, NS2 (NEP), PA, PB1, PB1-F2 and PB2 (Ghedin et al., 2005, Large-scale sequencing of human influenza reveals the dynamic nature of viral genome evolution. *Nature* 437: 1162-1166).

5.2. Antigens.

The antigens are those from the infectious disease for which one or more vaccines has been prepared, having identifiable sequences that may contain specific signature sequences. The signature sequences may comprise one or more amino acid sequence variations within an antigenic portion of the antigen, including subtype differences, immune escape forms, or drug resistant forms. The differences may include posttranslational modifications of the antigen. In the case of influenza A, the antigens are H1, H2, H3, H4, H6, H7, H8, H9 H10 H11 H12, H13, H14, H15 or H16 and 9 different neuraminidase subtypes N1 N2 N3 N4 N5 N6 N7 N8 or N9, as well as the nucleoprotein (NP), M1, M2, NS1, NS2 (NEP), PA, PB1, PB1-F2 and PB2.

5.3. Epitopes.

Epitope mapping, the determination of epitopes, uses processes known to those skilled in the arts and may include any methods known such as protease digestion/mass spectroscopy, spot membrane, phage peptide panning, monoclonal antibodies, hydrogen/deuterium exchange and/or crystallography in order to determine distinctive signature or fingerprint antigens (Morris (ed) Epitope Mapping Protocols, Humana Press, 1996; Joys and Schodel 1991. Infect. Immune. 59: 3330-3332; Hioe et al., 1990 J. Virol. 64: 6246-6251; Kaverin et al. 2002, J. Gen. Virol. 83: 2497-2505; Hulse et al. 2004, J. Virol. 78: 9954-9964; Kaverin et al. 2007, J. Virol. 81:12911-12917; Garcia et al., 2004, Hydrogen/deuterium exchange mass spectrosmetry for investigating protein-ligand interactions, ASSAY and Drug Development Technologies 2: 81-91; Kaverin et al., 2007, Epitope mapping of the hemagglutininin molecule of a highly pathogenic H5N1 influenza virus by using monoclonal antibodies, J. Virol. 81: 12911-12917; Hoffman et al., 2005, Role of specific hemagglutinin amino acids in the immunogenicity and protection of H5N1 influenza virus vaccines, PNAS 102: 12915-12920). T-cell epitope determination (Walden, 1996, Current Opinion in Immunology 8: 68-74) and computer programs such as Predict7 (Carmenes et al. 1989 Biochem. Biophys. Res. Comm 159: 687-693) and Pepitope (Mayrose et al., 2007. Bioinformatics 23: 3244-3246) or PepScan (Carter 1994, Epitope mapping of a protein using the Geysen (PEPSCAN) procedure. *Methods Mol Biol*. 1994; 36:207-23; Philpott et al., 1989, Neutralizing epitopes of the H5 hemagglutinin from a virulent avian influenza virus and their relationship to pathogenicity, J. Virol. 63: 3453-3458). Similar forms or homologous eiptopes can be determined as described by Deem and Pan, 2009 (The epitope regions of H1-subtype influenza A with application to vaccine efficacy, Protein Engineering and Selection 22: 543-546) by aligning sequences using amino acid sequence alignment algorithms such as ClustalW or by alignment of three-dimensional structure using "homology modeling" (Nayeem et al., 2006, A comparative study of available software for high-accuracy homology modeling: From sequence alignments to structural models, Protein Sci 15: 808-824).

A fingerprint or signature antigen, and/or epitope within the antigen, is one that is present in one form of a vaccine, and different by at least one or more amino acids, or absent in another form, and such, that antibodies produced recognize the difference. A fingerprint or signature antigen, and/or epitope within the antigen, may include their posttranslational modifications which may be present in one form and altered or absent in another also such that antibodies recognize the difference.

Variations and immune escape examples have been published by several authors (Caton et al., 1982, The antigenic structure of the influenza virus A/PR/8/34 hemagglutinin (H1 subtype, Cell 982:417-27; Ferguson et al., 2003, Ecological and immunological determinants of influenza evolution, Nature 422: 428-433; Drescher et al., 1993, Comparative investigation of the hemagglutinin epitopes of influenza virus A/Brazil/11/78 (H1N1). and its escape variants, J Virol Methods., 42:75-88; Hensley et al., 2009, Hemagglutinin receptor binding avidity drives influenza A virus antigenic drift. Science 326: 734-736; Table 1), and new variants can be rapidly determined by comparing previous years amino acids sequences, such as within the hemagglutinin, with new sequences, within the well-known and defined epitope regions. The highly neutralizing epitopes of influenza hemagglutinin are designated Sa, Sb, Ca and Cb (Caton et al., 1982, The antigenic structure of the influenza virus A/PR/8/34 hemagglutinin (H1 subtype, Cell 982:417-27), where the "S" refers to strain specific antigenic determinants, and the "C" refers to constant antigenic determinants.

TABLE 1

EXAMPLES OF INFLUENZA HEMAGGLUTININ EPITOPE OR ANTIGENIC ESCAPE MUTANTS

| ANTIGEN | MUTATION | Epitope | REFERENCE |
| --- | --- | --- | --- |
| Hemagglutinin A/Puerto Rico/8/1934 H1N1 | aa 158 E to K aa 246 E to G aa 156 E to K | Sa/Sb N/A Sb | Hensley et al., 2009, Hemagglutininin receptor binding avidity drives influenza A virus antigenic drift, Science 326: 734-728. EKEGSYPKLKNS [SEQ ID NO: 001] |

TABLE 1-continued

EXAMPLES OF INFLUENZA HEMAGGLUTININ EPITOPE OR ANTIGENIC ESCAPE MUTANTS

| ANTIGEN | MUTATION | Epitope | REFERENCE |
|---|---|---|---|
| Hemagglutinin A/Vietnam/ 1203/04 H5N1 | | | Kaverin et al., Epitope mapping of the hemagglutinin molecule of a highly pathogenic H5N1 influenza virus using monoclonal antibodies. J Virol 81: 12911-12917 |

5.4. Posttranslational Modifications for Antigens and Epitopes

Viral proteins may include posttranslational modifications whereby structural and/or functional non-peptidal biosynthetic covalent modifications of the polypeptide are formed. Postranslational modifications may include additions of phosphates, acetate, amines, lipids, sialic acid and carbohydrates. Carbohydrate structures, such as Gal alpha 1-3 Gal beta 1-4GlcNAc-R (termed the alpha-gal epitope) on viral glycoproteins is of interest because of the large amounts of natural antibody (anti-Gal) produced in humans against this epitope (Henion et al., 1997, Synthesis of alpha-gal epitopes on influenza virus vaccines, by recombinant alpha 1,3 galactosyltransferase, enables the formation of immune complexes with the natural anti-Gal antibody. *Vaccine* 15:1174-82). Because not all vaccines may contain glycosylated antigens, glycosylation of an antigen and/or a particular epitope may constitute a signature or fingerprint signature that can be used to distinguish an immune response by comparing the immune response to glycosylated and non-glycosylated counterparts. Likewise, sialic acids may constitute an antigenic portion variable among vaccines (Suzuki, 1993, Variation of influenza viruses and their recognition of the receptor sialo-sugar chains, *Yakugaku Zasshi,* 113: 556-78) and may be used as a diagnostic signature sequence.

5.5. Antibody-Based Assays.

Antibody assays are well known to those skilled in the arts and include enzyme-linked immunosorbent assays (ELISAs), immunoblots, protein arrays and many others (Ed Harlow and David Lane, Antibodies, A Laboratory Manual. Cold Spring Harbor Press, 1988, 731 pp). Antibody based assays allow the determination of the presence of antibodies (Cheng et al., 2008, Serologic and genetic characterization analysis of a highly pathogenic influenza virus (H5N1) isolated from an infected man in Shenzhen, J. Med. Virol. 80: 1058-1064; Katz et al., 1999, Antibody response in individuals infected with avian influenza A (H5N1) virus and detection of anti-H5 antibody among household and social contacts. J. Infect. Dis. 180: 1763-1770; Rowe et al., 1999, detection of antibody to avian influenza A (H5N1) virus in human serum using a combination of serologic assays, J. Clin. Microbiol. 37: 937-943). Antibody tests test for the presence of antibodies to a particular antigen, or portion of an antigen or specific epitope. Multiple formats exist, and either an antigen, an antibody, or capture antibody or capture ligand may first be adhered to a substrate, exposing it in a manner that allows a secondary exposure which may contain either the antibodies, antigen, or complex thereof, together with the necessary reporter and or detector, respectively, to bind to the antigen (Ed Harlow and David Lane, Antibodies, A Laboratory Manual. Cold Spring Harbor Press, 1988, 731 pp). By specifically detecting the presence of antibodies and their relative amount, knowledge of immunization to a particular parasite or infectious disease such as an influenza virus, either through immunization of one or more vaccines and vaccine antigens, or through natural exposure, can be ascertained. Various bodily fluids may contain antibodies to influenza, including blood (whole, serum or plasma), saliva, urine or (Ed Harlow and David Lane, Antibodies, A Laboratory Manual. Cold Spring Harbor Press, 1988, 731 pp; Urnovitz et al., 1999, Urine Antibody Tests: New Insights into the Dynamics of HIV-1 Infection Clinical Chemistry 45: 1602-1613; Vazquez et al., 2007, Kinetics of antibodies in sera, saliva, and urine samples from adult patients with primary or secondary dengue 3 virus infections, International Journal of Infectious Diseases 11: 256-262), or other mucus membranes such as the nasopharynx, bronchia or lungs.

In testing for antibody responses, tests for IgM are particularly useful for early testing because they constitute an early antibody response to infectious diseases, although IgG generally have a greater data base of well-described epitopes and persist longer. Immunoglobulin capture such as the "IgM capture" assays have been used for infectious disease exposure (Shaikn et al., 2007, Development of a novel, rapid, and sensitive immunochromatographic strip assay specific for west nile virus (WNV) IgM and testing of its diagnostic accuracy in patients suspected of WNV infection, Clin. Chem. 53: 2031-2034; Song, WO/2008/020293, West Nile virus envelope (e) protein antigen and immunoassay). However, these tests do not distinguish among multiple antigens with varying epitopes originating from one or more vaccines, nor among posttranslational modifications of the vaccine antigens.

6. FIGURE LEGENDS

FIG. 1A (top) shows an arrangement of different components in a strip test design and examples of positive (both bands present), negative (test band absent), and invalid (no control band) test results.

Figure 1B:

FIG. 1B (Bottom) shows tabular results of the test strip. The positive test results are suggestive of influenza immunity as the IgM levels are at or above the established cut-off level. Invalid results indicate that the test must be repeated. rFLU, recombinant influenza antigen; Mab, monoclonal antibody.

Figures 2A, 2B:
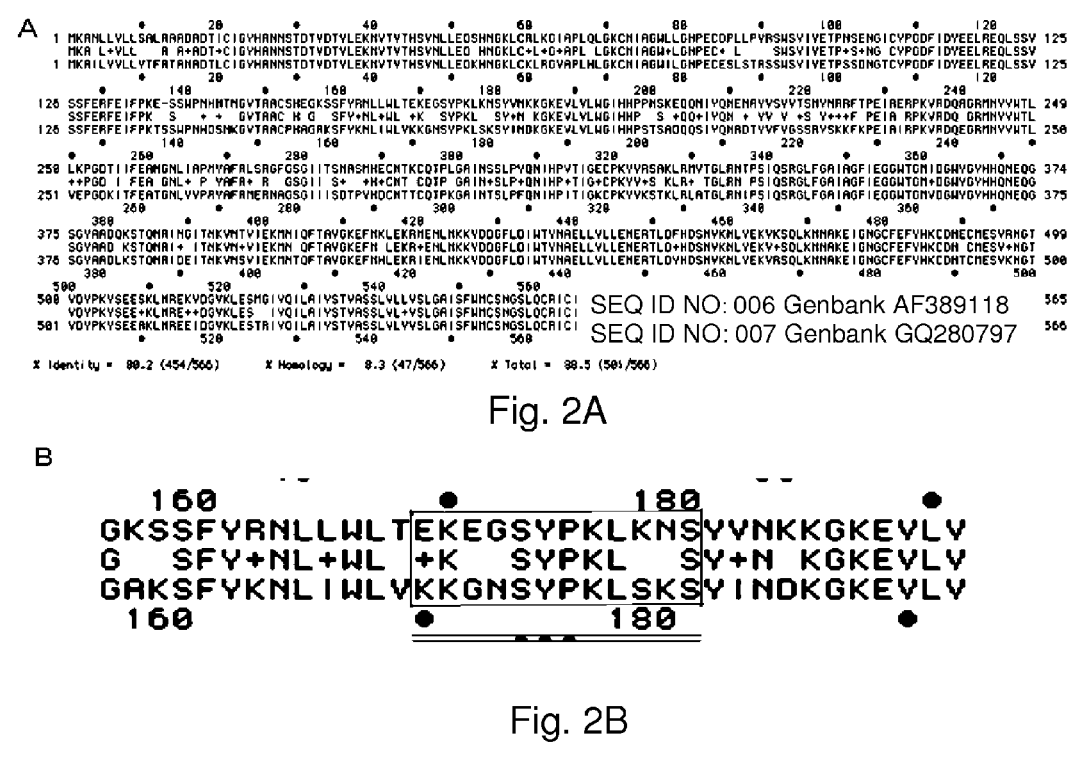

FIGS. 2A and 2B shows a determination of an epitope region of a sequence based on known epitopic regions. FIG. 2A shows a comparison of GenBank Accession number AF389118; top sequence) with the Genbank Accession number GQ280797 (bottom sequence) using DNA Strider (Douglas, 1995, DNA Strider. An inexpensive sequence analysis package for the Macintosh, *Mol Biotechnol* 3:37-45; middle sequence shows completely homologous regions) for which the hemagglutinin has with a known epitope map (Xu et al., 2010, FIG. 1). FIG. 2B shows an enlargement of the Sa epitope region from Xu et al., 2010, with a double underline for the Sa region, and a box drawn around the corresponding region in GenBank Accession number AF389118, identifying the sequence EKEGSYP-KLKNS [SEQ ID NO: 001]. The sequence can be paired with variants or escape mutants to distinguish the immune response between two vaccines.

Figures 3A, 3B, 3C:

FIGS. 3A, 3B and 3C show a modification of an epitope for use in a strip assay determining the response to one or more epitopes. FIG. 3A shows an example of a generalized structure of a peptide which may be recombinantly produced, consisting of the antigenic epitope, optionally a spacer peptide, a tag epitope, optionally a spacer peptide, a protease cleavage site (downward arrow shows cleavage location), optionally a spacer peptide, and a peptide to facilitate purification. FIG. 3B shows the wild type Sa epitope from Hensley et al., 2009 and corresponding amino acids for the generalized structure above, the FLAG epitope, a thrombin cleavage site (for removal of the purification peptide) and a hexahistidine peptide to facilitate purification, with spacer peptides GGG, shown in smaller type in between. FIG. 3C shows the same structure in B with an escape variant of the Sa epitope (E to K mutation in bold).

FIG. 4 shows the tabular results of a test strip with two representative set of finger print peptide sequences for two epitopes (E1 and E2) of H1 hemagglutinins, where the first epitope is described in FIG. 3B and the second epitope is described in FIG. 3C. The results are shown for 3 different patients. Patient 1 is positive for both hemagglutinin epitopes and therefore has been exposed to both types. Patient 2 is positive only for E1. Patient 3 is positive for only E2.

7. DETAILED DESCRIPTION OF THE PREFERRED EMBODIMENTS

In order to more fully illustrate the invention, the following examples are provided.

7.1. Example 1: An Immunochromatographic Strip Assay for IgM Capable for Determination of Successful Vaccination Patients will demonstrate an early antibody response of the IgM type during the first 4 days post vaccine immunization or illness, and nearly all patients will have detectable IgM antibodies by 7 to 8 days thereafter. Influenza-specific serum IgG is detectable by 3 weeks postinfection/inoculation. The virus itself is usually no longer detectable by the time influenza-specific serum IgM appears, although both IgM and IgG may persist for more than a year.

Both the ELISA and the strip format assay can use the same principle and the same antigens. A solid-phase immunochromatographic strip technology to qualitatively detect the presence of antibodies in human serum or plasma has been devised (Shaikh et al., Development of a novel, rapid, and sensitive immunochromatographic strip assay specific for West Nile Virus (WNV) IgM and testing of its diagnostic accuracy in patients suspected of WNV infection, Clin. Chem. 53: 2031-2034) and has been compared with ELISA assays (Tardei et al., 2000, Evaluation of immunoglobin M (IgM) and IgG enzyme immunoassays in serologic diagnosis of West Nile virus infection. J Clin Microbiol 38:2232-2239; Martin et al., 2000, Standardization of immunoglobin M capture enzyme-linked immunosorbent assays for routine diagnosis of arboviral infections. J Clin Microbiol 38:1823-1836; Malan et al., 2004, Evaluation of commercial West Nile virus immunoglobulin G (IgG) and IgM enzyme immunoassays show the value of continuous validation. J Clin Microbiol 42:727-733).

The test herein uses one or more specific influenza antigens such as the hemaggutinin, produced in one or more expression systems, such as a bacterium (e.g., *Escherichia coli*), producing non-glycosylated antigens, or using an insect cell/baculovirus system (Wei et al., 2008, Comparative Efficacy of Neutralizing Antibodies Elicited by Recombinant Hemagglutinin Proteins from Avian H5N1 Influenza Virus, J. Virol., 82: 6200-6208), with or without hexahistidine tag, producing glycosylated antigens (Merten et al., (eds) 2001, Recombinant protein production with prokaryotic and eukaryotic cells; A comparative view on host physiology, Kluwer Academic Publishers; Villaverde and Mattanovich, 2007, Recombinant protein production in the new millennium, Microb. Cell Fact. 6: 33 and references therein). Goat-antihuman IgM is biotinylated (biot-IgM) and a mouse monoclonal IgG anti-antigen antibody is conjugated onto colloidal gold particles (detector component). All 3 reagents are then dispensed onto the polyester pad and lyophilized. Streptavidin is immobilized onto a nitrocellulose (Sartorius) membrane strip at the test-band site. Rabbit antimouse IgG-Fc is immobilized at the control-band site. When the specimen is dispensed into the sample well, it passes through the membrane, which contains antigen, detector, and biot-IgM antibodies. The influenza IgM in the patient sample then forms a tertiary detector/antigen/IgM complex. The formed complex then migrates through the reaction strip and is captured at the test area. Excess, unreacted detector flows through the strip and is captured in the control area. The reactant concentrations are adjusted and optimized by analysis of calibrators, made from pooled influenza-positive sera, so that the test should produce a positive signal at influenza IgM Index value 1.1 of a commercially available IgM Capture ELISA device (Gentaur, Influenza Elisa Kit; comparator device) and negative results below that number.

Examples of positive, negative, and invalid test results are shown in FIG. 1B. Visible pinkish-purple horizontal bands appear in the test area if the concentration of the influenza IgM antibodies in the human serum sample is above the cutoff concentration in relation to the comparator device. A pinkish-purple band in the control area indicates that the test is working properly, and such a band must always appear, irrespective of the influenza IgM concentration, for the test to be considered valid.

7.2. Example 2: Selection of One or More Antigenic Epitope Peptides for Influenza H1N1 Hemagglutinin Vaccination Tests Antigens used for determining successful immunization are the antigens of a vaccine for which the test is specifically designed to assess. Thus, if a vaccine used a particular hemagglutinin, such as that of Genbank Accession number GQ280797, then the same hemaggutinin can be used to test for vaccination. If more than one vaccine is to be tested for within a single patient, specific areas of the antigen must be selected. The comparison of antigens that are present in different vaccines is based upon knowledge of the current vaccine compositions for which testing is desired. Antigen epitope peptides are selected based upon known antigenic sights, such as Sa, Sb, Ca, and Cb, based on epitope mapping. Prior epitope maps may be used, such as that described by Xu et al., 2010 (Structural basis of preexisting immunity to the 2009 H1N1 pandemic influenza, Science 328: 357-360) in order to determine the epitopic region of a new antigen. Hensley et al., 2009 have described escape mutants of an H1N1 influenza. The complete protein sequence of that hemagglutinin (GenBank Accession number AF389118) is compared with the Genbank Accession number GQ280797 for which the hemagglutinin has with a known epitope map (Xu et al., 2010, FIG. 1). The comparison of these two proteins, using the algorithm for DNA Strider (Douglas, 1995, DNA Strider. An inexpensive sequence analysis package for the Macintosh, *Mol Biotechnol* 3:37-45), is shown in FIGS. 2A and 2B. The homologous region is determined by amino acid homology, and the epitope of the sequence in question, EKEGSYPKLKNS [SEQ ID NO: 001], ascertained. A comparative test for vaccination by the escape mutant, which could occur with a vaccine made after the escape variant was isolated, can be performed using the escape mutant epitope, EKKGSYP-KLKNS [SEQ ID NO: 002] described by Hensley et al., 2009 (amino acid variant shown in bold).

7.3. Example 3: Construction of Peptides for IgG Immunochromatographic Strip Assays In order to modify the immunochomatographic strip assay to accommodate IgG, the epitope peptides must be tagged with an epitope tag in order to be recognized by a gold-conjugated detector antibody that is not recognized by an anti-human IgG biotinylated capture antibody. The test herein uses one or more specific fragments of recombinant influenza antigens (signature epitopes, such as those from Table 1, also described in the Example above) that are expressed as a fusion protein with specific antibody tags (e.g., epitope tags such as FLAG (DYKDDDDK) [SEQ ID NO: 003] or myc (EQKLISEEDL) [SEQ ID NO: 004] Jarvik and Telmer, 1998, Epitope tagging, Annual Review of Genetics, 32: 601-618), in one or more expression systems, such as a bacterium (Merten et al., (eds) 2001, Recombinant protein production with prokaryotic and eukaryotic cells; A comparative view on host physiology, Kluwer Academic Publishers; Villaverde and Mattanovich, 2007, Recombinant protein production in the new millennium, Microb. Cell Fact. 6: 33 and references therein). An diagram of a suitable peptide construct and representative peptides for Sa epitopes and a specific corresponding escape mutant of the same epitope is shown in FIGS. 3A, 3B and 3C.

7.4. Example 4: A Multivalent Immunochromatographic Strip Assay for IgG Capable of Distinguishing Patients Immunized with Different Hemagglutinins Variants The test herein uses one or more specific fragments of recombinant influenza antigens (signature epitopes, such as those from Table 1) that are expressed as a fusion protein with specific antibody tags (epitope tags such as FLAG (DYKDDDDK) [SEQ ID NO: 003] or myc (EQKLISEEDL) [SEQ ID NO: 004] Jarvik and Telmer, 1998, Epitope tagging, Annual Review of Genetics, 32: 601-618), in one or more expression systems, such as a bacterium (*Escherichia coli*; with or without hexahistidine (HHHHHH)-tag) [SEQ ID NO: 005], producing non-glycosylated antigens, or using an insect cell/baculovirus system (Wei et al., 2008, Comparative Efficacy of Neutralizing Antibodies Elicited by Recombinant Hemagglutinin Proteins from Avian H5N1 Influenza Virus, J. Virol., 82: 6200-6208), with or without hexahistidine tag, producing glycosylated antigens (Merten et al., (eds) 2001, Recombinant protein production with prokaryotic and eukaryotic cells; A comparative view on host physiology, Kluwer Academic Publishers; Villaverde and Mattanovich, 2007, Recombinant protein production in the new millennium, Microb. Cell Fact. 6: 33 and references therein), as described above and depicted in FIGS. 3A, 3B and 3C. Separate parallel strips may be constructed with each of the particular antigens. Goat-antihuman IgG is biotinylated (biot-IgG) and a non-crossreactive mouse monoclonal IgG anti-TAG antibody (i.e., not recognized by the goat anti-human IgG) is conjugated onto colloidal gold particles (detector component). All 3 reagents are then dispensed onto the polyester pad and lyophilized. Streptavidin is immobilized onto a nitrocellulose (Sartorius) membrane strip at the test-band site. Rabbit antimouse IgG-Fc is immobilized at the control-band site. When the specimen is dispensed into the sample well, it passes through the membrane, which contains antigen, detector, and biot-IgG antibodies. The influenza IgG in the patient sample then forms a tertiary detector/antigen/IgG complex. The formed complex then migrates through the reaction strip and is captured at the test area. Excess, unreacted detector flows through the strip and is captured in the control area. The reactant concentrations are adjusted and optimized by analysis of calibrators, made from pooled influenza-positive sera, so that the test should produce a positive signal at influenza IgG Index value 1.1 of a commercially available IgM Capture ELISA device (Gentaur, Influenza Elisa Kit; comparator device) and negative results below that number.

Examples of multivalent positive and negative results are shown in FIG. 4. Visible pinkish-purple horizontal bands appear in the test area if the concentration of the influenza IgG antibodies in the human serum sample is above the cutoff concentration in relation to the comparator device. A pinkish-purple band in the control area indicates that the test is working properly, and such a band must always appear, irrespective of the influenza IgG concentration, for the test to be considered valid. In FIG. 4 results of a test strip with two representative set of finger print peptide sequences for two epitopes (E1 and E2) of H1 hemagglutinins, where the first epitope is described in FIG. 3B and the second epitope is described in FIG. 3C. The results are shown for 3 different patients. Patient 1 is positive for both hemagglutinin epitopes and therefore has been exposed to both types. Patient 2 is positive only for E1. Patient 3 is positive for only E2. If it is known that all three patients have been given two types of vaccines, one corresponding to E1 and one corresponding to E2, then the additional interpretation is that in patient 1, both vaccines were successful, and that in patients two and three, only one of the two vaccines were successful. Knowledge of this success can guide patients, especially the elderly, to seek additional vaccination if necessary, and can guide healthcare workers and those seeking to understand the efficacy of vaccines which vaccines are successful and which are not, even when the patients have received more than one vaccine.

The various aspects of the disclosure may be combined and subcombined to represent all consistent combinations and subcombinations without departing from the scope of the invention. The invention is limited by neither the specific embodiments of the specification, nor the particular scope of the claims, but rather is to be treated as encompassing the full scope of each aspect disclosed, and the various combinations and permutations, which do not depart from the enabled disclosure herein.

What is claimed is:

1. A testing method for presence of antibodies to an antigen from a host, comprising:
   (a) providing:
      (1) a reactant layer, into which are absorbed a ternary complex comprising:
         the antigen,
         a host antibody binding agent comprising at least one of an anti-host immunoglobulin IgM antibody and an anti-host immunoglobulin IgG antibody, bound to a ligand, and
         a detector comprising a non-host anti-antigen IgG antibody conjugated to colloidal particles;
      (2) a test strip, in fluid communication with the reactant layer at a portion thereof, to which is immobilized:
         a ligand binding agent at a test area; and
         an anti-non-host IgG antibody immobilized at a control area,
         the test area being spaced more proximate to the reactant layer than the control area; and
      (3) a sample well,
   (b) placing a serum specimen from a host in the sample well;
   (c) selectively forming a quaternary complex of:
      host antigen-specific antibody in the serum specimen;
      the detector;
      the antigen; and
      the host antibody binding agent;
   (d) capturing the quaternary complex which migrates through the test strip using the immobilized ligand binding agent at the test area; and
   (e) capturing the complex comprising the antigen and the detector, unbound to host antigen-specific antibodies, which migrates through the test strip past the test area, by using the immobilized anti-non-host IgG antibody,
   to thereby indicate a presence of the host antigen-specific antibodies by an indication at the test area and validity of the test by an indication at the control area.

2. The method according to claim 1, wherein:
   the ligand is biotin and the ligand binding agent is streptavidin;
   the colloidal particles are colloidal gold particles;
   the host antibody binding agent bound to a ligand comprises biotinylated goat-antihuman IgM antibody;
   the non-host anti-antigen IgG antibody comprises mouse monoclonal anti-antigen IgG antibody;
   the anti-non-host IgG antibody immobilized at the control area comprises rabbit anti-mouse IgG-Fc;
   the reactant layer comprises a polyester pad;
   the test strip comprises a nitrocellulose membrane;
   the test strip comprises an elongated strip, on which the reactant layer is situated on one side;
   the sample well is on top of the reactant layer;
   a flow control layer is provided between the reactant layer and the test strip;
   the test area and control area are sequentially disposed distant from the test strip; and
   the antigen, the host antibody binding agent bound to a ligand, and the detector are provided in at least one solution,
   further comprising:
   providing an absorbent pad in fluid communication with the test strip disposed on an opposite side of the control area from the reactant layer, wherein the absorbent pad induces a bulk fluid flow from the reactant layer to the absorbent pad; and
   dispensing and subsequently lyophilizing the at least one solution on the reactant layer.

3. A testing method for presence of antibodies to a particular antigen from a host, comprising:
   providing a reactant layer, having the particular antigen, at least one of an anti-host immunoglobulin IgM antibody and an anti-host immunoglobulin IgG antibody bound to a ligand, and a non-host anti-antigen IgG antibody conjugated to a detector;
   forming a complex by adding serum containing host antibodies to the particular antigen, wherein the host antibodies and the non-host anti-antigen IgG antibody bind the particular antigen, and the at least one of an anti-host immunoglobulin IgM antibody and an anti-host immunoglobulin IgG antibody bound to a ligand binds the host antibodies;
   migrating the complex on a strip toward a first region having an immobilized ligand binding agent which binds and ceases migration of the at least one of an anti-host immunoglobulin IgM antibody and an anti-host immunoglobulin IgG antibody bound to a ligand and any complexes including the at least one of an anti-host immunoglobulin IgM antibody and an anti-host immunoglobulin IgG antibody bound to a ligand;
   migrating an unbound residual portion of the complex past the first region to a second region having immobilized anti-non-host IgG antibody immobilized at a control area, which binds the non-host anti-antigen IgG antibody and any complexes including the non-host anti-antigen IgG antibody,
   wherein,
      if the host antibodies have a sufficient affinity for the antigen and are present in sufficient quantity, a complex comprising the antigen, the host antibodies, and the at least one of an anti-host immunoglobulin IgM antibody and an anti-host immunoglobulin IgG antibody bound to a ligand and the non-host anti-antigen IgG antibody conjugated to the and detector are retained in the first region by the immobilized ligand binding agent for detection based on the presence of the detector, and
      if the host antibodies have insufficient affinity for the antigen or are not present in sufficient quantity, a complex comprising the antigen, and the non-host anti-antigen IgG antibody conjugated to the detector, will migrate past the first region and be retained at the second region by the immobilized anti-non-host IgG antibody for detection based on the presence of the detector.

4. A testing method for presence of host antigen-specific antibodies to an antigen from a host, comprising:
   (a) providing:
      (1) a reactant layer, into which are absorbed the antigen, an anti-host immunoglobulin antibody bound to a ligand, and a detector comprising a non-host anti-antigen antibody conjugated to colloidal particles;
      (2) a test strip configured to permit migration of a fluid and to provide fluid communication with the reactant layer at a portion thereof, to which is immobilized a ligand binding agent at a test area and anti-non-host antibody immobilized at a control area, the test area being spaced more proximate to the reactant layer than the control area; and
      (3) a sample well in fluid communication with the test strip at a portion thereof, (b) placing a fluid serum specimen from a host in the sample well, and permitting the fluid serum specimen to migrate into and through the test strip;

(c) permitting host antigen-specific antibodies in the fluid serum specimen to selectively form a quaternary host antigen-specific antibody/detector/antigen/anti-host immunoglobulin antibody complex with the detector, antigen, and anti-host immunoglobulin antibody;

(d) capturing quaternary host antigen-specific antibody/detector/antigen/anti-host immunoglobulin antibody complex which migrates through the test strip using the immobilized ligand binding agent at the test area; and (e) capturing the detector and antigen, unbound to antigen-specific host antibodies, which migrates through the test strip past the test area using the immobilized anti-non-host antibody, to thereby indicate a presence of the host antigen-specific antibodies by an indication at the test area and validity of the test by an indication at the control area.

5. The method according to claim 4, wherein the ligand is biotin and the ligand binding agent is streptavidin.

6. The method according to claim 4, wherein the colloidal particles are gold particles.

7. The method according to claim 4, wherein anti-host immunoglobulin antibody bound to the ligand is an anti-host immunoglobulin IgM-antibody bound to the ligand, and the concentrations of antigen, anti-host immunoglobulin IgM-antibody bound to the ligand, the detector, immobilized ligand binding agent and immobilized anti-non-host antibody are provided, based on calibration with pooled sera from other hosts which have responded to an immunization with the antigen by production of the host antigen-specific antibodies, to produce a positive indication at an IgM Index value of at least 1.1 of an IgM Capture ELISA device and a negative indication results below an IgM Index value of 1.1 of the IgM Capture ELISA device.

8. The method according to claim 4, wherein the antigen is an influenza hemagglutinin.

9. The method according to claim 4, wherein the antigen is an influenza hemagglutinin produced by the genetically engineered bacterium.

10. The method according to claim 4, wherein the antigen is a glycosylated antigen produced in an insect cell/baculovirus system.

11. The method according to claim 4, wherein the anti-host immunoglobulin antibody bound to a ligand comprises biotinylated goat-antihuman IgM antibody.

12. The method according to claim 4, wherein the non-host anti-antigen antibody comprises a mouse monoclonal IgG anti-antigen antibody.

13. The method according to claim 12, wherein the anti-non-host antibody immobilized at the control area comprises a rabbit anti-mouse IgG-Fc.

14. The method according to claim 12, wherein the mouse monoclonal IgG anti-antigen antibody is conjugated onto colloidal gold particles.

15. The method according to claim 4, wherein the antigen, the anti-host immunoglobulin antibody bound to the ligand, and the detector are dispensed as at least one solution on the reactant layer and subsequently lyophilized.

16. The method according to claim 4, wherein the reactant layer comprises a polyester pad.

17. The method according to claim 4, wherein the test strip comprises a nitrocellulose membrane.

18. The method according to claim 4,
wherein the test strip comprises an elongated strip, on which the reactant layer is situated on one-side of the test strip, and the test area and control area are sequentially disposed distant from the test strip along a migration path of the fluid through the test strip, the sample well is on top of the reactant layer, and between the reactant layer and the test strip is disposed at least one flow control layer, further comprising:

(f) providing an absorbent pad in fluid communication with the test strip disposed on an opposite side of the control area from the reactant layer with respect to the migration path of the fluid through the test strip; and (g) inducing a bulk migration of fluid from the reactant layer to the absorbent pad.

19. The method according to claim 4, wherein:

the ligand is biotin and the ligand binding agent is streptavidin;

the colloidal particles are colloidal gold particles;

the anti-host immunoglobulin antibody bound to a ligand comprises biotinylated goat-antihuman IgM antibody;

the non-host anti-antigen antibody comprises mouse monoclonal anti-antigen IgG antibody; and the anti-non-host antibody immobilized at the control area comprises rabbit anti-mouse IgG-Fc, further comprising:

(f) providing an absorbent pad in fluid communication with the test strip disposed on an opposite side of the control area from the reactant layer with respect to a path of fluid migration through the test strip, wherein the absorbent pad induces a bulk fluid flow from the reactant layer to the absorbent pad; and (g) dispensing as at least one solution and subsequently lyophilizing the antigen, the anti-host immunoglobulin antibody bound to the ligand, and the detector on the reactant layer, wherein the test strip comprises an elongated strip, on which the reactant layer is situated on one side, the test area and control area are sequentially disposed along a fluid migration path from the sample well in the test strip, and the sample well is on top of the reactant layer, and between the reactant layer and the test strip is disposed at least one flow control layer.

20. The method according to claim 3, wherein:

the ligand is biotin and the ligand binding agent is streptavidin;

the non-host anti-antigen IgG antibody comprises a monoclonal antibody;

the anti-non-host IgG immobilized at the control area comprises an IgG-Fc;

the reactant layer is situated over a flow control layer on one side of a strip, with a sample well on top of the reactant layer;

the first region and the second region are sequentially disposed distant from the reactant layer; and an absorbent pad is disposed on an opposite side of the second region from the reactant layer, which induces a bulk fluid flow from the reactant layer to the absorbent pad; and the antigen, the at least one of the anti-host immunoglobulin IgM antibody and the anti-host immunoglobulin IgG antibody bound to the ligand, and the detector are lyophilized in the reactant layer.

* * * * *

SEQUENCE LISTING

<160> NUMBER OF SEQ ID NOS: 8

<210> SEQ ID NO 1
<211> LENGTH: 12
<212> TYPE: PRT
<213> ORGANISM: Influenza A virus

<400> SEQUENCE: 1

Glu Lys Glu Gly Ser Tyr Pro Lys Leu Lys Asn Ser
1               5                   10

<210> SEQ ID NO 2
<211> LENGTH: 12
<212> TYPE: PRT
<213> ORGANISM: Influenza A virus

<400> SEQUENCE: 2

Glu Lys Lys Gly Ser Tyr Pro Lys Leu Lys Asn Ser
1               5                   10

<210> SEQ ID NO 3
<211> LENGTH: 8
<212> TYPE: PRT
<213> ORGANISM: Artificial Sequence
<220> FEATURE:
<223> OTHER INFORMATION: FLAG epitope specific antibody tag

<400> SEQUENCE: 3

Asp Tyr Lys Asp Asp Asp Asp Lys
1               5

<210> SEQ ID NO 4
<211> LENGTH: 10
<212> TYPE: PRT
<213> ORGANISM: Artificial Sequence
<220> FEATURE:
<223> OTHER INFORMATION: myc epitope specific antibody tag

<400> SEQUENCE: 4

Glu Gln Lys Leu Ile Ser Glu Glu Asp Leu
1               5                   10

<210> SEQ ID NO 5
<211> LENGTH: 6
<212> TYPE: PRT
<213> ORGANISM: Artificial Sequence
<220> FEATURE:
<223> OTHER INFORMATION: hexahistidine coding and affinity purification
      tag

<400> SEQUENCE: 5

His His His His His His
1               5

<210> SEQ ID NO 6
<211> LENGTH: 565
<212> TYPE: PRT
<213> ORGANISM: Influenza A virus

<400> SEQUENCE: 6

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Lys Cys Asn Ile Ala Gly Trp Leu Leu Gly
65                  70                  75                  80

```
Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495
```

-continued

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 7
<211> LENGTH: 566
<212> TYPE: PRT
<213> ORGANISM: Influenza A virus

<400> SEQUENCE: 7

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Ile
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

```
Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 8
<211> LENGTH: 42
<212> TYPE: PRT
<213> ORGANISM: Artificial Sequence
<220> FEATURE:
<223> OTHER INFORMATION: Wild type Sa epitope (Hensley et al. 2009),
      FLAG epitope tag, Thrombin cleavage site (AGPR-SLX), Hexahistidine
      tag
<220> FEATURE:
<221> NAME/KEY: misc_feature
<222> LOCATION: (33)..(33)
<223> OTHER INFORMATION: Xaa can be any naturally occurring amino acid

<400> SEQUENCE: 8

Glu Lys Glu Gly Ser Tyr Pro Lys Leu Lys Asn Ser Gly Gly Gly Asp
1               5                   10                  15

Tyr Lys Asp Asp Asp Asp Lys Gly Gly Gly Ala Gly Pro Arg Ser Leu
            20                  25                  30

Xaa Gly Gly Gly His His His His His His
        35                  40
```